US008273538B2

(12) United States Patent  
Rappaport et al.

(10) Patent No.: US 8,273,538 B2  
(45) Date of Patent: Sep. 25, 2012

(54) BLOOD MONOCYTE CD163 EXPRESSION AS A BIOMARKER IN HIV-1 INFECTION AND NEUROAIDS

(75) Inventors: Jay Rappaport, Somers Point, NJ (US); Tracy Fischer-Smith, Horsham, PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 433 days.

(21) Appl. No.: 12/301,796

(22) PCT Filed: May 25, 2007

(86) PCT No.: PCT/US2007/069716  
§ 371 (c)(1),  
(2), (4) Date: Nov. 21, 2008

(87) PCT Pub. No.: WO2008/019186  
PCT Pub. Date: Feb. 14, 2008

(65) Prior Publication Data  
US 2010/0291595 A1 Nov. 18, 2010

Related U.S. Application Data

(60) Provisional application No. 60/809,014, filed on May 26, 2006.

(51) Int. Cl.  
C12Q 1/70 (2006.01)  
C12Q 1/68 (2006.01)  
G01N 33/53 (2006.01)  
G01N 33/567 (2006.01)

(52) U.S. Cl. .......... 435/7.1; 435/6.1; 435/7.2; 435/7.21; 435/5

(58) Field of Classification Search ........................ None  
See application file for complete search history.

(56) References Cited

U.S. PATENT DOCUMENTS

2002/0155995 A1 10/2002 Moestrup et al.  
2003/0077576 A1 4/2003 Trial et al.

FOREIGN PATENT DOCUMENTS

WO WO02074789 9/2002

OTHER PUBLICATIONS

Novak et al. Characterization of monocyte subtypes in the allergic form of atopic eczema/dermatitis syndrome. Allergy 2002, vol. 57, pp. 931-935.*
Moniuszko et al. Enhanced frequencies of CD14++CD16+, but not CD14+CD16+, peripheral blood monocytes in severe asthmatic patients. Clinical Immunology 2009, vol. 130, pp. 338-346.*
Roberts et al. CD163 identifies a unique population of ramified microglia in HIV encephalitis. Journal of Neuropathology and Experimental Neurology 2004, vol. 63, No. 12, pp. 1255-1264.*
Pulliam et al. Unique monocyte subset in patients with AIDS dementia. The Lancet 1997, vol. 349, pp. 692-695.*
Ziegler-Heitbrock, L. The CD14+ CD16+ monocytes: their role in infecction and inflammation. Journal of Leukocyte Biology 2007, vol. 81, pp. 584-592.*
Haigwood, N. Predictive Value of Primate Models for AIDS. AIDS Reviews 2004, vol. 6, pp. 187-198.*
Tippett et al. Differential Expression of CD163 on Monocyte Subsets in Healthy and HIV-1 Infected Individuals. PLoS ONE, May 2001, vol. 6, Issue 5, e19968, p. 1-11.*
Kim, et al. CD-163 Identifies Perivascular Macrophages in Normal and Viral Encephalitic Brains and Potential Precursors to Perivascular Macrophages in blood American Journal of Pathology, Mar. 2006, 168(3):822-834.
Tubiana et al., Long-lasting recovery in CD4 T-cell function and viral-load reduction after highly active antiretroviral therapy in advanced HIV-1 disease, Lancet, Oct. 1998, 351 (9117): 1682-1686.
International Search Report, Application No. PCT/US 07/69716 dated May 25, 2007.
FISCHER_SMITH et al., CNS invasion by CD14+/CD16+ peripheral blood-derived monocytes in HIV dementia: perivascular accumulation and reservoir of HIV infection, Journal of NeuroVirology, 2001, vol. 7, pp. 528-541.
FISCHER_SMITH et al., CD163/CD16 Coexpression by Circulating Monocytes/Macrophages in HIV: potential biomarkers for HIV Infection and AIDS Progression, AIDS Research and Human Retroviruses, vol. 24, No. 3, 2008, pp. 417-421.
FISCHER_SMITH et al. Monocyte/macrophage trafficking in acquired immunodeficiency syndrome encephalitis; Lessons from human and nonhuman primate studies, Journal of NeuroVirology 2008, 14; pp. 318-326.

* cited by examiner

*Primary Examiner* — Louise Humphrey  
(74) *Attorney, Agent, or Firm* — Caesar, Rivise, Bernstein, Cohen & Pokotilow, Ltd.

(57) ABSTRACT

The invention provides a method for detecting CD163+/CD16+ cell population in peripheral blood mononuclear cells in a biological sample from a subject infected with HIV-1 which comprises contacting the biological sample with an anti-CD163 antibody, so that levels of CD163+/CD16+ peripheral blood mononuclear cells in the biological sample can be quantified. The method of the present invention is particularly useful for monitoring the course of HIV-1 infection and/or HIV Encephalopathy

7 Claims, 8 Drawing Sheets

BLOOD MONOCYTE CD163 EXPRESSION AS A BIOMARKER IN HIV-1 INFECTION AND NEUROAIDS

CROSS-REFERENCE TO RELATED APPLICATIONS

This application claims benefit of U.S. Provisional Application 60/809,014, filed May 26, 2006, incorporated herein by reference in its entirety.

STATEMENT REGARDING FEDERALLY SPONSORED RESEARCH OR DEVELOPMENT

The invention described herein was supported in part by NIH/NINDS grant IRO I NSO47031. The United States government has certain rights in the invention.

BACKGROUND OF THE INVENTION

1. Field of Invention

This invention relates to measurements of monocyte CD163, a monocyte/macrophage-specific scavenger receptor for hemoglobin-haptoglobin complex, mean fluorescence intensity and frequency measurements in blood which is an important surrogate marker for clinical management of HIV-1 infected individuals. This marker may be used to predict disease progression, viral load and changes in viral load, and may be important in diagnosis and or risk assessment relative to CNS and other neurological manifestations of HIV infection.

2. Description of Related Art

Monocytes are a heterogeneous population of cells capable of differentiation into a variety of mature cell types including different subsets of macrophages, myeloid endritic cells and osteoclasts. The invention provides that alterations in monocyte populations in human immunodeficiency virus type 1 (HIV-1) infection, correlate to expression of two cell surface markers, CD16 and CD163. While all monocytes express CD14, a lipopolysaccharide (LPS) receptor, (Ziegler-Heitbrock H W, Passlick B, Flieger D. The monoclonal anti monocyte antibody My4 stains B lymphocytes and two distinct monocyte subsets in human peripheral blood. Hybridoma 1988, 7:521-527.), the less frequent CD16+ monocyte subset is considered more mature, with characteristics similar to mature macrophages (Ziegler-Heitbrock H W, Fingerle G, Strobel M, et al. The novel subset of CD14+/CD16+ blood monocytes exhibits features of tissue macrophages. Eur J Immunol 1993, 23:2053-2058.). Increased frequency of CD14+/CD16+ monocytes in the setting of HIV-1 infection have been observed by several groups (Allen J B, Wong H L, Guyre P M, Simon G L, Wahl S M. Association of circulating receptor Fc gamma Rill-positive monocytes in AIDS patients with elevated levels of transforming growth factor-beta. J Clin Invest 1991, 87: 1773-1779; Locher C, Vanham G, Kestens L, et. al. Expression patterns of Fc gamma receptors, HLA-DR and selected adhesion molecules on monocytes from normal and HIV infected individuals. Clin Exp hnmuno/ 1994, 98: 115-122; Thieblemont N, Weiss L, Sadeghi H M, Estcourt C, Haeffner-Cavaillon N. CD14lowCD16high: a cytokine-producing monocyte subset which expands during human immunodeficiency virus infection. Eur J Immuno/ 1995, 25:3418-3424; Pulliam L, Gascon R, Stubblebine M, McGuire D, McGrath M S. Unique monocyte subset in patients with AIDS dementia. Lancet 1997, 349:692-695.). Further, while HIV-1 infected patients naive to highly active antiretroviral therapy (HAART) have expanded CD16+ monocytes and express higher levels of proinflammatory cytokines, they also show increased levels of the antiinflammatory cytokine, ILIO (Amirayan-Chevillard N, Tissot-Dupont H, Capo C, et aJ. hnpact of highly active antiretroviral therapy (HAART) on cytokine production and monocyte subsets in HIV infected patients. Clin Exp hnmunol 2000, 120: 107-112.). While it was not determined in that study which monocyte subset (CD14+/CD16+ or CD14++/CD16) was responsible for ILIO production, the results suggest that there may be an association between the CD16+ monocyte subset and IL10 expression. Comparable to the TH1 versus TH2 cytokine profiles expressed by T cells, macrophages can exhibit analogous polarization. While the proinflammatory, IL12 producing Macrophage-1 are involved in antigen presentation and memory T cell activation, IL10 producing, alternatively activated macrophages, MΦ-2, are primarily involved in housekeeping functions, i.e. phagocytosis, tissue remodeling and immune suppression. Both populations have their appropriate functions; however, polarization to a MΦ-2 phenotype could have important immune consequences in the setting of HIV-1 infection by adversely affecting the ability of the host immune system to adequately control virus as well as other opportunistic pathogens implicated in AIDS pathogenesis. It is likely that alterations in monocyte populations promote a TH2 cytokine shift and contribute to the pathogenesis of HIV infection.

Expression of CD163, a scavenger receptor for hemoglobin-haptoglobin (hg-hp) complex, is reportedly exclusive to monocytes and specific tissue macrophages in humans and has been used to phenotypically identify Mt-2 (Zwadlo G, Voegeli R, Osthoff K S, Sorg C. A monoclonal antibody to a novel differentiation antigen on human macrophages associated with the downregulatory phase of the inflammatory process. Exp Cell Biol 1987, 55:295-304; Sulahian T H, flogger P, Wainer A E, et al. Human monocytes express CD163, which is upregulated by IL-10 and identical to p155. Cytokine 2000, 12:1312-1321; Lau S K, Chu P G, Weiss L M. CD163: a specific marker of macrophages in paraffinembedded tissue samples. Am J Clin Patho/2004, 122:794-801; Nguyen T T, Schwartz E J, West R B, Warnke R A, Arber D A, Natkunam Y. Expression of CD163 (Hemoglobin Scavenger Receptor) in Normal Tissues, Lymphomas, Carcinomas, and Sarcomas Is Largely Restricted to the Monocyte Macrophage Lineage. Am J Surg Patho/2005, 29:617-624.). Considering the significance of macrophages in HIV-1 infection and disease progression and the potential role of MΦ-2 in skewing the host immune response to an anti-inflammatory phenotype, peripheral blood from HIV-1 infected and seronegative individuals was examined for alterations in CD163+ monocyte subsets and assessed their correlation with viral load and AIDS progression. While CD163 expression is associated with the macrophage Φ-2 phenotype, it is unclear if CD163+ monocytes are a circulating form of the MΦ-2. In support of this notion IL10 secreting monocytes have recently been demonstrated to exhibit an increased frequency of CD163 expression (Prasse A, Germann M, Pechkovsky D V, et al. IL-10-producing monocytes differentiate to alternatively activated macrophages and are increased in atopic patients. J Allergy Clin Immuno/2007, 119:461 171.). Since CD16 expression on monocytes suggests a more mature macrophage phenotype, it is possible and even likely that the CD163+/CD16+ monocytes are circulating forms of the MΦ-2 or are predisposed to further differentiate into the MΦ-2.

HIV-1 dementia complex (HIVD) affects approximately 10% of adults and almost all children infected with HIV-1 with acquired immunodeficiency syndrome (AIDS). HIV encephalitis (HIVE), the pathology of HIVD, is characterized by an accumulation of perivascular macrophages, multinucleated giant cells, and nodular lesions with areas of focal necrosis and white matter thinning (Rostad S W, Sumi S M, Shaw C M et al. Human immunodeficiency virus (HIV) infection in brains with AIDS-related leukoencephalopathy. AIDS Res Hum Retroviruses. 1987; 3:363-373; 2. Pumarola-Sune T, Navia B A, Cordon-Cardo C et al. HIV antigen in the brains of patients with the AIDS dementia complex. An Neurd. 1987; 21:490-496; 3. Budka H, Costan G, Cristina S et al. Brain pathology induced by infection with the human immunodeficiency virus (HIV). A histological, immunocytochemical, and electron microscopical study of 100 autopsy cases. Acta Neuropathol (Berl). 1987; 75: 185-198.). The Trojan Horse' model was originally proposed, where circulating HIV-1 infected macrophages seed the central nervous system (CNS) early in HIV-I infection with transmission to other cells within the CNS compartment, leading to neuronal loss and CNS dysfunction (Meltzer M S, Skillman D R, Gomatos P J et al. Role of mononuclear phagocytes in the pathogenesis of human immunodeficiency virus infection. Annu Rev Immunol. 1990; 8:169-194.). An alternative hypothesis is that the initial productive infection in the CNS is cleared by the immune system, with a second invasion in the setting of AIDS. This model was proposed by Pullam et al. (Pulliam L, Gascon R, Stubblebine M. et al. Unique monocyte subset in patients with AIDS dementia. Lancet. 1997; 349:692-695.), where increased levels of CD16+ monocytes were observed in circulation in AIDS, particularly in the setting of dementia. Based on the activation of this circulating monocyte subset, increased invasiveness of these cells was proposed to playa role in the pathogenesis of HIVD. Previously, we identified two populations of activated MPs in the CNS of patients with HIVE (Fischer-Smith T, Croul S, Sverstiuk A E et al. CNS invasion by CD14+/CD16+ peripheral blood-derived monocytes in HIV dementia: perivascular accumulation and reservoir of HIV infection. J. Neurovirol. 2001; 7(6):528-41.). Recently, CD163, a monocyte/macrophage-specific scavenger receptor for hemoglobinhaptoglobin complex, was reported to be expressed in the CNS by perivascular macrophages but not by resident microglia in human brain. The inventors utilized this disparity in the expression pattern of CD163 by perivascular macrophages versus microglia to further characterize the mononuclear phagocytes (MPs) in the CNS in HIVE. Briefly, we found a significant number of CD163+ macrophages accumulating perivascularly and within the brain parenchyma in patients with HIVE. Many of the CD163+ cells observed in the parenchyma of patients with HIVE have a ramified morphology and likely represent CNS engraftment of perivascular macrophages that have migrated into the brain parenchyma and taken on microglial characteristics. The majority of CD163+ cells is also shown by co-localization studies to harbor productive HIV-1 infection and as such, is a significant source of virus in the CNS. Further, CD163 co-localizes significantly with CD16 in HIVE CNS. Here we show that uninfected and S1Vmac251 infected Rhesus macaques with and without SIV encephalopathy (SIVE) have alterations in peripheral blood monocyte activation/maturation markers by flow cytometry and this correlates with viral load and CNS disease.

All references cited herein are incorporated herein by reference in their entireties.

BRIEF SUMMARY OF THE INVENTION

The invention provides a method for detecting CD163+ peripheral blood monocytes in a biological sample which comprises contacting the biological sample with an anti-CD163 antibody, so that levels of CD163+ peripheral blood monocytes in the biological sample can be quantified. The method of the present invention is particularly useful for monitoring the course of HIV-1 infection and/or HIV Encephalopathy.

The invention provides a method for detecting the presence of CD163+/CD16+ monocytes in a biological sample comprising contacting the biological sample with an anti-CD14 antibody, contacting the biological sample with an anti-CD16 antibody, contacting the biological sample with an anti-CD163 antibody, detecting the presence of anti-CD14, anti-CD16, and anti-CD163 antibodies bound, wherein the quantity of anti-CD14 antibody bound is a measure of the total monocytes present, and the quantity of anti-CD16 and anti-CD163 bound is an indication of the CD163+/CD16+ monocytes present in the biological sample. The invention provides this method wherein the biological sample is a member selected from the group consisting of whole blood, serum, plasma, cerebrospinal fluid, saliva, urine, spinal fluid, synovial fluid, amniotic fluid and cranial fluid, and lymphocyte or cell culture supernatants. The invention provides this method wherein the biological sample is from an HIV positive subject.

The invention provides a method for monitoring the course of disease in an HIV positive subject which comprises, obtaining a first sample from the subject, determining from the first sample the fraction of CD163+/CD16+ monocytes in peripheral blood mononuclear cells, at a different time, obtaining a second sample from the subject, determining from the second sample the fraction of CD163+/CD16+ monocytes in peripheral blood mononuclear cells, wherein a difference in the measured fraction of CD163+/CD16+ monocytes in peripheral blood mononuclear cells determined from the first sample and the second sample being indicative of the course of disease.

The invention provides a method for determining the prognosis of an HIV infected individual, comprising, obtaining a sample from the subject, determining from the sample the fraction of CD163+/CD16+ monocytes in a population of peripheral blood mononuclear cells, comparing the measured levels to a fraction of CD163+/CD16+ monocytes in a population of peripheral blood mononuclear cells in healthy seronegative individuals, and determining the prognosis of the HIV-infected individual.

The invention provides a method for determining a prognosis in an HIV-1 positive subject comprising, determining the fraction of CD163+/CD16+ monocytes in peripheral blood mononuclear cells of the subject, an increase in the fraction of CD163+/CD16+ monocytes over a base line level being indicative of a an unfavorable prognosis for the individual.

The invention provides a method for determining the level of CNS invasion by HIV-1 virus in HIV-1 positive subjects comprising, obtaining a sample from the subject, determining the fraction of CD163+/CD16+ monocytes in peripheral blood mononuclear cells of the subject, wherein an increase in the fraction of CD163+/CD16+ monocytes over a base line level being indicative of CNS invasion by said virus. The invention further provides a method wherein the sample is a member selected from the group consisting of whole blood, serum, plasma, cerebrospinal fluid, saliva, urine, spinal fluid, synovial fluid, amniotic fluid and cranial fluid, and lymphocyte or cell culture supernatants.

The invention provides a method of diagnosing a disease condition related to HIV in a patient comprising, obtaining a blood sample from the patient, determining from the sample the fraction of CD163+/CD16+ monocytes in peripheral blood mononuclear cells, presenting such measure, and applying the measure of the fraction of CD163+/CD16+ monocytes in peripheral blood mononuclear cells selectively as a diagnostic evaluation of a disease condition related to HIV.

The invention provides a method for predicting disease progression in an HIV-I positive subject by the steps comprising obtaining a sample from the subject, determining from the sample the fraction of CD163+/CD16+ monocytes in peripheral blood mononuclear cells, comparing the measured levels to a mean fraction of CD163+/CD16+ monocytes in peripheral blood mononuclear cells value, and predicting disease progression of the HIV infected individual.

The invention provides a method for diagnosis of HIV encephalopathy by the steps comprising obtaining a sample from the subject, determining from the sample the fraction of CD163+/CD16+ monocytes in peripheral blood mononuclear cells, comparing the measured levels to a mean fraction of CD163+/CD16+ monocytes in peripheral blood mononuclear cells value, and determining whether the subject has HIV encephalopathy, wherein the fraction of CD163+/CD16+ monocytes in peripheral blood mononuclear cells levels above the base line value correlates to the diagnosis of HIV encephalopathy.

The invention provides a method for monitoring the viral load of an HIV-1 positive individual by the steps comprising obtaining a sample from the subject, determining from the sample the fraction of CD163+/CD16+ monocytes in peripheral blood mononuclear cells, and comparing the measured levels to a mean fraction of CD163+/CD16+ monocytes in peripheral blood mononuclear cells value, wherein the fraction of CD163+/CD16+ monocytes in peripheral blood mononuclear cells levels over a base line level correlates to an increase in HIV-1 viral load in the individual.

The invention provides a method for determining the risk of disease progression in an HIV infected individual by the steps comprising obtaining a sample from the subject, determining from the sample the fraction of CD163+/CD16+ monocytes in peripheral blood mononuclear cells, and comparing the measured levels to a mean fraction of CD163+/CD16+ monocytes in peripheral blood mononuclear cells value, wherein the fraction of CD163+/CD16+ monocytes in peripheral blood mononuclear cells levels over a base line level correlates to an increased risk of disease progression in an HIV infected individual.

The invention provides a method for determining the risk of development of HIV encephalopathy in an HIV infected subject by the steps comprising obtaining a sample from the subject, determining from the sample the fraction of CD163+/CD16+ monocytes in peripheral blood mononuclear cells, comparing the measured levels to a mean fraction of CD163+/CD16+ monocytes in peripheral blood mononuclear cells value, and determining the risk of development of HIV encephalopathy in an HIV infected subject, wherein the fraction of CD163+/CD16+ monocytes in peripheral blood mononuclear cells levels above the base line value correlates to an increased risk of development of HIV encephalopathy in the subject, further wherein the fraction of CD163+/CD16+ monocytes in peripheral blood mononuclear cells levels above the base line value are an indication that the HIV infected subject should be treated with antiretroviral therapy.

The invention provides a diagnostic kit for the detection of CD163 and/or CD16 antigens comprising a container comprising at least one antibody which is a member of the group consisting of an antibody which specifically binds CD16 protein, an antibody which specifically binds CD163 protein, and combinations thereof. The invention provides a diagnostic kit further comprising a solid support selected from the group consisting of wells of reaction trays, test tubes, polystyrene beads, strips, membranes and microparticles. The invention provides a diagnostic kit further comprising a label selected from the group consisting of enzymes, radioisotopes, fluorescent compounds and chemiluminescent compounds. The invention provides a diagnostic kit wherein the enzymatic label is horseradish peroxidase. The invention provides a diagnostic kit further comprising a hapten and labeled anti-hapten system wherein the hapten is conjugated to a labeled murine monoclonal antibody.

The invention provides a method for predicting the risk of a decrease in CD4+ T cell count in an HIV infected individual by the steps comprising obtaining a sample from the subject, determining from the sample the fraction of CD163+/CD16+ monocytes in peripheral blood mononuclear cells, and comparing the measured levels to a mean fraction of CD163+/CD16+ monocytes in peripheral blood mononuclear cells value, wherein the fraction of CD163+/CD16+ monocytes in peripheral blood mononuclear cells levels over a base line level correlates to the risk of a decrease in CD4+ T cell count in an HIV infected individual. The invention provides a method for monitoring the effect of antiretroviral therapy on the CD4+ T cell count in an HIV infected individual by the steps comprising obtaining a sample from the subject, determining from the sample the fraction of CD163+/CD16+ monocytes in peripheral blood mononuclear cells, and comparing the measured levels to a level after treatment of the individual with anti-retroviral therapy, wherein a decrease in the fraction of CD163+/CD16+ monocytes in peripheral blood mononuclear cells levels after antiretroviral therapy correlates to a decrease in viral load, an increase in CD4+ cell counts, clinical stability, and/or lower risk of HIV encephalitis/dementia in an HIV infected individual.

BRIEF DESCRIPTION OF SEVERAL VIEWS OF THE DRAWINGS

The invention will be described in conjunction with the following drawings wherein:

FIG. 1A and FIG. 1D show frontal white matter from a SIV seronegative Rhesus macaque. FIG. 1B and FIG. 1E are SIVmac251 infection without encephalopathy. FIG. 1C, FIG. 1F and FIG. 1G are from SIVE. The top row (FIG. 1A, FIG. 1B, and FIG. 1C) illustrates parenchyma. FIG. 1D, FIG. 1E and FIG. 1F show blood vessels. FIG. 1G shows a microglial nodule. All panels are shown at 40× magnification.

The percent frequency of CD16+ monocytes is significantly higher in patients with mid HIV-1 viral loads relative to seronegative donors, but this difference was not significant when comparing the high viral load and seronegative groups (FIG. 5A). This is most likely the result of a low number of donors in the high viral load group (n=3). In support of this notion, combining the mid and high viral load groups such that the groups are HIV-1 (seronegative), HIV-1+ with undetectable viral load (suppressed) and HIV-1+ with a detectable viral load (mid-high) results in an even lower P value when comparing the seronegative donors and those with detectable virus (FIG. 5B). The percent monocyte frequency identified by CD14 expression that co-express CD163 and CD16 is increased in donors with mid and high viral loads, compared to volunteers with virus suppression and seronegative donors (FIG. 5C). Similar to the CD16+ monocyte subset, we observed a decrease in the frequency of CD163+/CD16+ monocytes in patients with virus suppression (FIG. 5C and FIG. 5D). This is not due solely to CD16 expression but also involves a lower percent frequency of CD163+ cells. A small decrease in CD163+ monocytes is observed approximately to the same degree among all groupings of HIV-1 infected individuals but is not significantly reduced as compared to seronegative individuals (data not shown). In contrast to our observations with the CD16+ monocyte subset, expansion of the CD163+/CD16+ monocyte subset in donors with high viral loads was significantly increased over seronegative controls (p<0.05) (FIG. 5C). Furthermore, the comparison between the fraction of the CD163+/CD16+ subset in donors with HIV-1 infection and mid viral load (FIG. 5C) and seronegative donors exhibited increased significance than when compared to CD16+ monocytes without CD163 (p<0.001 with CD163 vs p<0.05 without CD163 sub-typing). Combining the mid and high viral load groups results in a small increase in the median but does not improve the significance (FIG. 5D).

Figure 6:
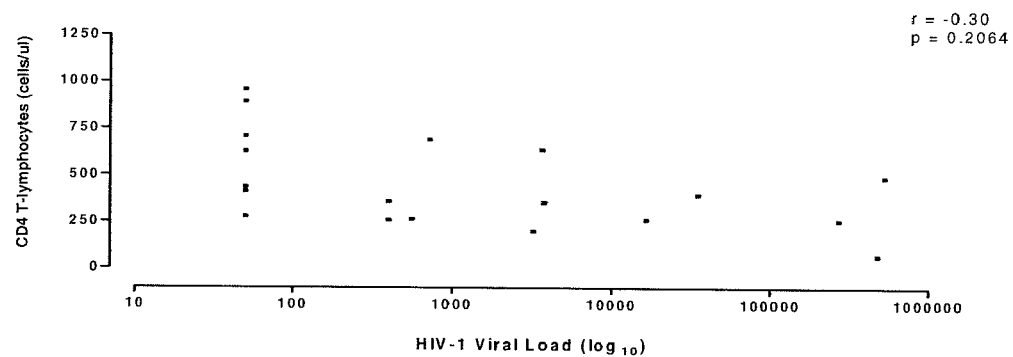
Figure 6:
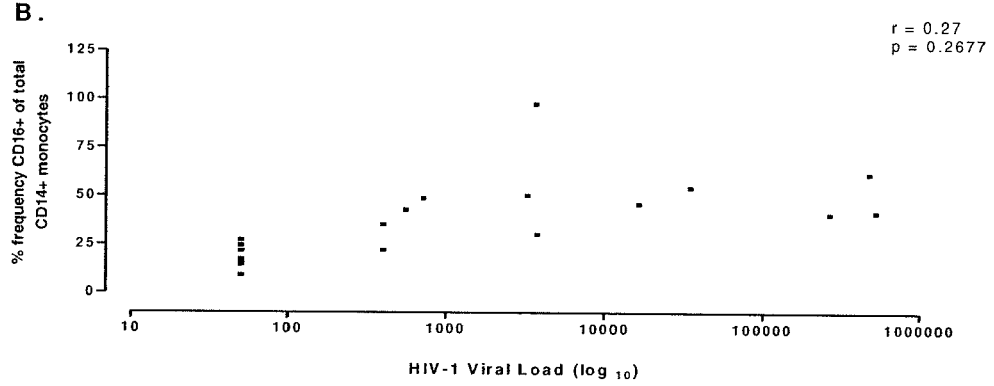
Figure 6:
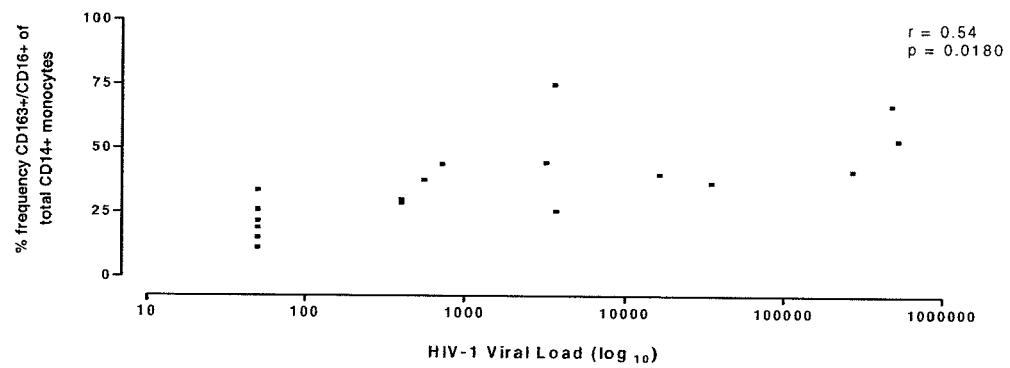

FIG. 6 illustrates that the percent frequency of CD163+/CD16+ monocytes correlates with viral load in HIV-1 infected individuals. A reduction in CD4+ T cells with increased viral load was observed, however, this correlation did not reach significance (FIG. 6A). Conversely, the percent frequency of CD14+/CD16+ monocytes appears to increase with increased viral burden, however, like CD4+ T cells, this relationship did not reach statistical significance (FIG. 6B). The frequency of CD163+/CD16+ monocytes also increases with viral load (FIG. 6C), however, unlike both CD4+ T cells and CD14+/CD16+ monocytes, the correlation between the frequency of CD163+/CD16+ monocytes and viral burden is statistically significant (FIG. 6C), r=0.54; p=0.018, suggesting a relationship with virus production and the expansion of this monocyte subset.

Figure 7:
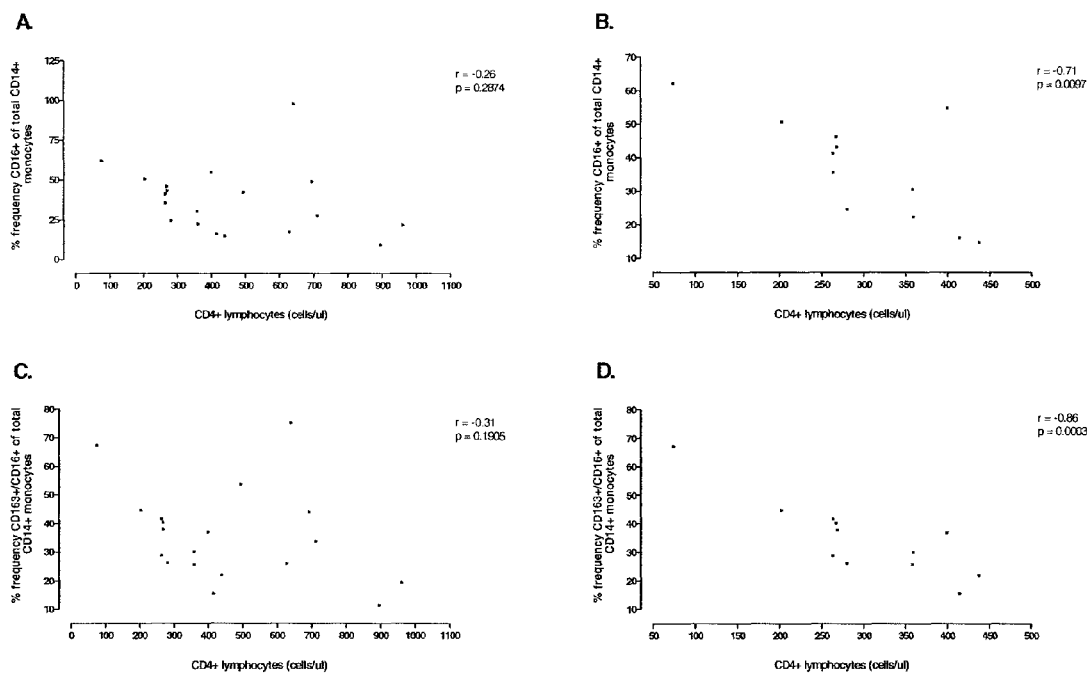

FIG. 7 illustrates that the expansion of both CD16+ monocyte subsets correlates with CD4+ T cell depletion. A trend toward a decrease in the absolute number of CD4+ T cells with increased CD16+ and CD163+/CD16+ monocyte frequencies was observed in all HIV-1 infected individuals, however this was not significant for either monocyte subset (FIG. 7A and FIG. 7C). Interestingly, patients with CD4+ T cell counts below 450 cells/0 show a significant inverse correlation between CD4+ T cells and CD16+ or CD163+/CD16+(FIG. 7B and FIG. 7D). While both monocyte subsets do correlate well with a loss of CD4+ T cells in HIV-1 infected persons with counts less than 450 cells/µ1, the correlation between CD163+/CD16+ monocyte subset frequency and CD4+ T cell loss is better than that seen with the CD16+ monocyte (compare FIG. 7A r=0.26 with C 0.31) as well as in those with CD4+ T cells below 450 cells/µ1 (compare FIG. 7B r=0.71 with FIG. 7D r=0.86).

Figure 8:
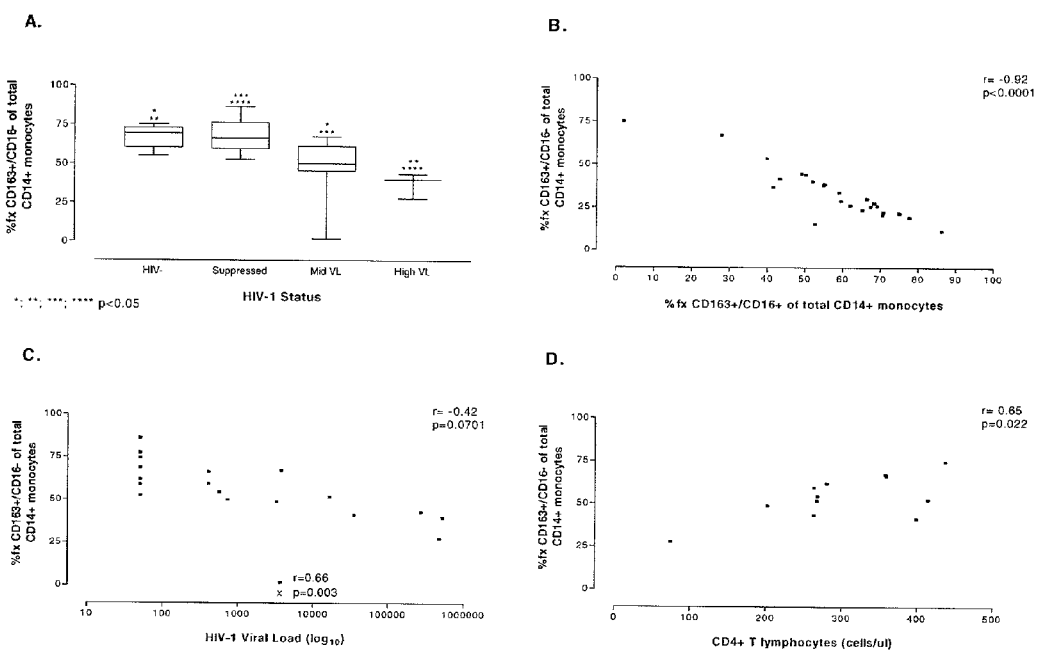

FIG. 8 illustrates that expansion of the CD163+/CD16+ monocyte subset may develop from CD163+/CD16− monocytes. The frequency of CD163+/CD16+ monocytes is greater in seronegative individuals and those with virus suppression than HIV-1 infected donors with mid or high viral loads (FIG. 8A). The frequency of CD163+/CD16− monocytes showed a strong inverse correlation with the frequency of CD163+/CD16+ monocytes (FIG. 8B). A strong trend toward a decrease of this monocyte subset with increased viral load (p=0.07) was observed among all HIV-1 infected individuals enrolled in this study (FIG. 8C). A highly significant inverse correlation was observed with r=0.66 and p=0.003 (FIG. 8C). A positive trend toward a greater number of CD4+ T cells was also observed with increased CD163+/CD16− monocyte frequency that is not statistically significant until CD4+ T cells drop below 450 cells/µl (FIG. 8D).

DETAILED DESCRIPTION OF THE INVENTION

The invention provides that the CD163+/CD16+ monocyte subset is significantly expanded in HIV-1 infected individuals with detectable viral loads when compared to HIV-1 infected individuals with virus suppression and healthy seronegative volunteers. The invention provides that expansion of this monocyte subset correlates significantly with increased virus production and CD4+ T cell depletion. The invention provides that CD163+/CD16+ monocytes play a direct or indirect role in virus expansion and/or CD4+ T cell loss and serve as a biomarker for HIV-1 infection and progression of AIDS. The invention provides that the expansion of a monocyte subset associated with viral load and/or CD4+ T cell loss, and therefore disease progression. Flow cytometric analysis of PBMC isolated from whole blood of HIV+ and seronegative volunteers revealed expansion in the frequency of CD16+ monocytes, identified by CD14 expression in patients with HIV-1 infection and detectable viral load when compared to those with virus suppression and seronegative individuals. This became more significant when comparing the frequency of CD163+/CD16+ monocytes among these groups, presumably through reduced variation within the CD16+ monocyte subset among donors in each grouping, suggesting a more consistent expansion of the CD163+/CD16+ subset among patients with detectable virus. The expansion of both CD16+ monocyte subsets correlates well with CD4+ T cell loss at counts below 450 cells/µl; however, this is more significant when weighed against expansion of the CD163+/CD16+ subset. While the total frequency of CD16+ monocytes increases, this increase is confined to the CD163+ monocyte subset. There is no increase in CD16 positivity within the CD163 subset (possibly a precursor to the Mg-1). Presumably, the variation in numbers of Mg-1 detracts from the value of the correlation between viral load and CD4+ T cell count. This is supported by lower p-value for the association of the fraction of CD16+/CD163+ versus CD6+ alone with viral load and CD4+ T cell count.

The invention provides that CD16+ monocytes are important to HIV-1 disease progression. CD16+ but not CD16− monocytes produce high levels of virus upon differentiation into macrophages and T cell interaction. Previously, the expansion of the CD16+ monocyte subset was demonstrated in patients with HIV-1/AIDS, with even greater expansion seen in patients with HIV-1 associated dementia (HIVD), subcortical dementia associated with significant accumulation of HIV-1 infected and uninfected activated macrophages, when compared to seronegative individuals (Ancuta P, Kunstman K J, Autissier P, et al. CD16+ monocytes exposed to HIV promote highly efficient viral replication upon differentiation into macrophages and interaction with T cells. Virology 2006, 344:267-276.). CD16+ monocytes exhibit features of tissue macrophages, are more phagocytic and express higher levels of inflammatory cytokines than CD16 monocytes (Scherberich J E, Nockher W A. Blood monocyte phenotypes and soluble endotoxin receptor CD14 in systemic inflammatory diseases and patients with chronic renal failure. Nephrol Dial Transplant 2000, 15:574-578). The invention provides that there is a significant accumulation of CD16+ perivascular macrophages and microglia in the CNS of patients with HIVE, the neuropathology of HIVD (Fischer-Smith T, Craul S, Sverstiuk A E, et al. CNS invasion by CD14+/CD16+ peripheral blood-derived monocytes in HIV dementia: perivascular accumulation and reservoir of HIV infection. Neuroviro/2001, 7:528-541). CD163 expression by CD16+ monocytes may contribute to the invasiveness of these cells as CD163 has been demonstrated to augment monocyte adherence to LPS or cytokine stimulated endothelial cells (Wenzel I, Roth J, Sorg C. Identification of a novel surface molecule, RM3/1, that contributes to the adhesion of glucocorticoid-induced human monocytes to endothelial cells. Eur J Immuno/1996, 26:2758-2763). We have found that the CD16+ cells that accumulate perivascularly and within the brain parenchyma in HIVE are largely CD163+. CNS accumulation of MΦ-2s perivascularly and within the parenchyma, the CNS (as well as other tissues) is a rich source of immunosuppressive cytokines in patients with HIVE. Neurocognitive impairment in HIV infection is associated with increased mortality. Furthermore, CSF and plasma Macrophage Colony Stimulating Factor (MCSF), upregulates CD16 expression on monocytes (Munn D H, Garnick M B, Cheung N K. Effects of parenteral recombinant human macrophage colony-stimulating factor on monocyte number, phenotype, and antitumor cytotoxicity in nonhuman primates. Blood 1990, 75:2042-2048) and promotes the differentiation of monocytes into MΦ2 (Ritter M, Buechler C, Langmann T, Orso E, Klucken J, Schmitz G. The scavenger receptor CD163: regulation, promoter structure and genomic organization. Pathobiology 1999, 67:257-261) has been correlated with shortened time to death in a cohort of patients with advanced HIV infection (Sevigny J J, Albert S M, McDermott M P, et al. An evaluation of neurocognitive status and markers of immune activation as predictors of time to death in advanced HIV infection. Arch Neuro/2007, 64:97-102). This is particularly intriguing in view of our results which demonstrate a correlation between the CD16+/CD163+ subset and viral load, and the inverse correlation with CD4+ T cell decline.

In addition to the correlation between CD1 63+/CD16+ monocytes with CD4+ T cell loss, the invention provides that CD163+/CD16+ monocyte subset expansion in HIV-1 infected individuals correlates strongly with viral load, regardless of past or present use of anti-retroviral therapy. While there is consensus that viral load is a prognostic indicator for progression toward AIDS, particularly in combination with CD4+ T cell count (Mellors et al., 1997), the correlation between viral load and CD4 decline is not a strong one (Rodriguez et al., 2006). Additional variables appear to affect the rate of CD4 decline among HIV infected persons. CD163+/CD16+ monocyte subset information is an interesting candidate with respect to the data distribution. While volunteers with low viral consistently had low frequencies of CD16+/CD1 63+ cells, patients with mid to high viral loads had a broad range of values. It is possible that the CD16+/CD163+ subset may provide better prognostic value alone or in combination with viral load information or in combination also with CD4+ T cell count. The expanded CD163+/CD16+ monocyte/macrophage subset seen in HIV-1 infected individuals with a detectable viral load coincides with a statistically significant decrease in the CD163+/CD16 subset, suggesting that the CD163+/CD16+ subset arises from the CD163+/CD16 subset. This may, at least in part, result from the altered cytokine environment promoted by the virus-host interactions. For example, MCSF production is up-regulated in HIV-1 infected monocyte-derived macrophages (MDM) and enhances the susceptibility of macrophages to infection (Kalter D C, Nakamura M, Turpin J A, et al Enhanced HIV replication in macrophage colony-stimulating factor-treated monocytes. J Immuno/1991, 146:298-306). Further, this increased susceptibility is suggested to occur through alterations in monocyte differentiation/activation by MCSF rather than any effect MCSF might have on the virus itself (Bergamini A, Perno C F, Dini L, et al. Macrophage colony-stimulating factor enhances the susceptibility of macrophages to infection by human immunodeficiency virus and reduces the activity of compounds that inhibit virus binding. Blood 1994, 84:3405-3412). Interestingly, in vitro treatment of primary monocytes promotes differentiation to CD163+ macrophages (Buechler C, Ritter M, Orso E, Langmann T, Klucken J, Schmitz G. Regulation of scavenger receptor CD163 expression in human monocytes and macrophages by pro- and antiinflammatory stimuli. J Leukoc Biol 2000, 67:97-103.) and has also been shown to up-regulate CD16 expression (Young D A, Lowe L D, Clark S C. Comparison of the effects of IL-3, granulocytemacrophage colony-stimulating factor, and macrophage colony-stimulating factor in supporting monocyte differentiation in culture. Analysis of macrophage antibody-dependent cellular cytotoxicity. J Immuno/ 1990, 145:607-615). Additionally, macrophages stimulated with MCSF produce high levels of IL10 but do not produce 1L12 (Smith W, Feldmann M, Londei M. Human macrophages induced in vitro by macrophage colony-stimulating factor are deficient in IL-12 production. Eur J Immuno/1998, 28:2498-2507) suggesting a role for MCSF in reducing inflammation and potentially promoting a MΦ-2 phenotype.

The frequency of total CD163+ monocytes was decreased in all patients with HIV-1 infection, regardless of viral suppression or burden, when compared to seronegative individuals (data not shown). The degree of frequency reduction was similar among all HIV+ groupings but was not significant between HIV+ and negative groups. This may be due to altered CD163 expression, increased trafficking of CD163+ monocytes/MΦ into tissues or shedding of CD163 into a soluble form of the molecule (sCD163).

The invention provides that the frequency of CD163+/CD16+ monocytes provides an earlier prognostic marker for the development of AIDS and HIV-1, and that the frequency of CD163+/CD16+ monocytes provides an earlier prognostic marker for the development of neurocognitive disorders associated with HIV/AIDS.

The inventors have found that there is significant accumulation of CD163+ macrophages located perivascularly and within the brain parenchyma of SIVmac251 infected Rhesus macaques with encephalopathy. Analysis of whole blood by flow cytometry reveals an increase in CD163 expression by circulating monocytes, as demonstrated by greater CD163 mean fluorescence intensity (MF1). CD163 MF1 correlates significantly with viral load (r=0.669, p=0.0024). The frequency of CD163hi/CD16+ is significantly higher in SW infected Rhesus macaques with high viral loads. This correlation is even more significant when comparing the frequency of CD163hi/CD16hi monocytes with viral load. CD16+ monocytes may be important to the development of HW-D as this subset is largely expanded in patients with AIDS/dementia Enhanced CD163 expression on CD16+ monocytes may contribute to the invasiveness of these cells as CD163 augments monocyte adherence to LPS or cytokine-stimulated cells. CD163hi/CD16+ monocytes correlate positively with viral load (r-=0.618, p=0.0124), with an even more significant correlation observed between the CD163hi/eD16hi subpopulation (r=0.81 7, p=0.0001). Together, these data provide support for the role of altered monocytes activation/maturation in the peripheral blood to the contribution of SIV neuropathogenesis and, potentially, HIVE. CD163 is an important biomarker in AIDS and NeuroAIDS.

The invention provides a method for monitoring the viral load of an HIV-1 positive individual which comprises determining the level of CD163+ cells in peripheral blood mononuclear cells of the subject, an increase in CD163+ cells over a base line level being indicative of increased HIV-1 viral load in the individual.

The invention provides a method for monitoring the viral load of an HIV-1 positive individual which comprises determining the level of CD163+/CD16+ cells in peripheral blood mononuclear cells of the subject, an increase in CD163+/CD16+ cells over a base line level being indicative of increased HIV-1 viral load in the individual.

The invention provides a method for monitoring the viral load of an HIV-1 positive individual which comprises determining the level of CD163/CD16+ cells in peripheral blood mononuclear cells of the subject, an increase in CD163/CD16+ cells over a base line level being indicative of increased HIV-1 viral load in the individual.

The invention is also a method for determining a prognosis in an HIV-1 positive subject which comprises determining the level of CD163+ and/or CD16+ cells in peripheral blood mononuclear cells of the subject, an increase in CD163+ and/or CD16+ cells over a base line level being indicative of a an unfavorable prognosis for the individual.

The invention is also directed to a method for predicting disease progression in an HIV-1 positive subject which comprises determining the level of CD163+ and/or CD16+ cells in peripheral blood mononuclear cells of the subject, an increase in CD163+ and/or CD16+ cells over a base line level being indicative of advanced disease.

The invention is also a method for determining the level of CNS invasion by virus in an HIV-I positive subjects comprising determining the level of CD163+ and/or CD16+ cells in peripheral blood mononuclear cells of the subject, an increase in CD163+ and/or CD16+ cells over a base line level being indicative of CNS invasion by said virus.

The invention is also a method for diagnosis of HIV encephalopathy which comprises determining the relative level of CD163+ and/or CD16+ cells in peripheral blood mononuclear cells of a subject, an increase in CD163+ and/or CD16+ cells over a base line level being indicative of the presence of HIV encephalopathy in the subject.

The invention provides a metric for beginning and continuing the treatment of an HIV-1 infected individual with antiretroviral therapy by which comprises determining the relative level of CD163+/CD16+ cells in peripheral blood mononuclear cells of a subject, an increase in CD163+/CD16+ cells over a base line level indicating the need for beginning and/or continuing the treatment of an HIV-1 infected individual with antiretroviral therapy. The CD163+/CD16+ cell levels are a more sensitive indicator than CD4+ T cell levels, and can indicate the need for beginning an/or continuing antiretroviral therapy before the CD4+ T cells reach 30 cells/µL.

The "base line" level of marker cells may be, for example, a control level ascertained from testing of PBMC from normal uninfected donors, or may be an earlier level sampled from the infected individual.

According to one embodiment, the cells are cultured in vitro, and comprise peripheral blood monocytes/macrophages. The cells are cultured according to well known techniques for culturing peripheral blood monocytes/macrophages.

Biological samples which are easily tested by the method of the present invention include human and animal body fluids such as whole blood, serum, plasma, cerebrospinal fluid, PBMC, saliva, urine, spinal fluid, synovial fluid, amniotic fluid and cranial fluid, and lymphocyte or cell culture supernatants. Biological samples may be collected from humans or non-human animals.

Target Antigens

A first embodiment of the present invention relates to an antibody that binds to a CD163 protein. A typical amino acid sequence of CD163 protein is shown in SEQ ID NO: 1 (Ritter M., Buechler C., Langmann T. and Schmitz G. Genomic organization and chromosomal localization of the human CD163 (M130) gene: a member of the scavenger receptor cysteine-rich superfamily. Biochem. Biophys. Res. Commun. 260 (2), 466-474 (1999)). That is, an antibody according to the first embodiment of the present invention is preferably an antibody that specifically binds to the CD163 polypeptide and variants, fragments, muteins, etc., thereof, and those proteins derived from this protein. It is known that humans have a diversity of allele mutations and those proteins with one or more amino acids substituted, deleted, inserted, or added are also included in the CD163 protein. However, it is not limited to these.

A typical amino acid sequence of CD16 protein is shown in SEQ ID NO: 2. (Arambum J, Azzoni L, Rao A. and Perussia B. Activation and expression of the nuclear factors of activated T cells, NFATp and NFATc, in human natural killer cells: regulation upon CD16 ligand binding. J. Exp. Med. 182 (3), 801-810 (1995)). That is, an antibody according to the first embodiment of the present invention is preferably an antibody that specifically binds to the CD16 polypeptide and variants, fragments, muteins, etc., thereof, and those proteins derived from this protein. It is known that humans have a diversity of allele mutations and those proteins with one or more amino acids substituted, deleted, inserted, or added are also included in the CD163 protein. However, it is not limited to these.

Fragments of the CD16 or CD163 protein may serve as the target antigen for the antibody binding. These antigen fragments may be about 6, 7, 8, 9, 10, 11, 12, 13, 14, 15, 16, 17, 18, 19, or 20 amino acids in length. The antigen fragments may by about 10, 20, or 100 amino acids in length. The antibody of the present invention may be either a polyclonal antibody or a monoclonal antibody. To specifically detect a high molecular weight soluble CD163 protein, it is desirable to use antibodies to certain limited epitopes and hence monoclonal antibodies are preferable. Molecule species are not particularly limited. immunoglobulins of any class, subclass or isotype may be used.

Antibodies and Antibody Compositions

Additionally, the present invention includes a purified antibody produced in response to immunization with CD163 and/or CD16, as well as compositions comprising this purified antibody.

Antibodies refer to single chain, two-chain, and multi-chain proteins and glycoproteins belonging to the classes of polyclonal, monoclonal, chimeric, and hetero immunoglobulins; it also includes synthetic and genetically engineered variants of these immunoglobulins. "Antibody fragment" includes Fab, Fab', F(ab')2, and Fv fragments, as well as any portion of an antibody having specificity toward a desired target epitope or epitopes. A humanized antibody is an antibody derived from a non-human antibody, typically murine, that retains or substantially retains the antigen-binding properties of the parent antibody but which is less immunogenic in humans, U.S. Pat. No. 5,530,101, incorporated herein by reference in its entirety.

An antibody composition of the present invention is characterized as containing antibody molecules that immunoreact with CD163 and/or CD16, or a related polypeptide of this invention, but is substantially free of antibodies that immunoreact with any other related protein.

In accordance with the present invention, immunoglobulins specifically reactive with CD16 related epitopes are provided. In accordance with the present invention, immunoglobulins specifically reactive with CD163 related epitopes are provided.

In accordance with the present invention, humanized immunoglobulins specifically reactive with CD16 related epitopes are provided. In accordance with the present invention, humanized immunoglobulins specifically reactive with CD163 related epitopes are provided.

An antibody composition of the present invention is typically produced by immunizing a laboratory mammal with an inoculum of the present invention and to thereby induce in the mammal antibody molecules having the appropriate polypeptide immunospecificity. The antibody molecules are then collected from the mammal and isolated to the extent desired by well known techniques such as, for example, by immunoaffinity chromatography. The antibody composition so produced can be used in, inter alia, the diagnostic methods and systems of the present invention to detect CD163 and/or CD16 in a body sample.

The antibody compositions of this invention induced by a polypeptide of this invention, including an oligomeric polypeptide and a polypeptide polymer, can be described as being oligoclonal as compared to naturally occurring polyclonal antibodies since they are raised to an immunogen (the relatively small polypeptide) having relatively few epitopes as compared to the epitopes mimicked by an intact CD163 and/or CD16 molecule. Consequently, receptors of this invention bind to epitopes of the polypeptide, whereas naturally occurring antibodies raised to the whole CD163 and/or CD16 molecule bind to epitopes throughout the CD163 and/or CD16 molecule and are referred to as being polyclonal.

Monoclonal antibody compositions are also contemplated by the present invention. A monoclonal antibody composition contains, within detectable limits, only one species of antibody combining site capable of effectively binding CD163 and/or CD16. Thus, a monoclonal antibody composition of the present invention typically displays a single binding affinity for CD163 and/or CD16 even though it may contain antibodies capable of binding proteins other than CD163 and/or CD16.

Suitable antibodies in monoclonal form, typically whole antibodies, can also be prepared using hybridoma technology described by Niman et al., Proc. Natl. Sci., U.S.A., 80:4949-4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a polypeptide of this invention.

Splenocytes are typically fused with myeloma cells using polyethylene glycol (PEG) 1500. Fused hybrids are selected by their sensitivity to HAT. Hybridomas secreting the receptor molecules of this invention are identified using the enzyme linked immunosorbent assay (ELISA).

A monoclonal antibody composition of the present invention can be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

The monoclonal antibody compositions produced by the above method can be used, for example, in diagnostic and therapeutic modalities wherein formation of a CD163 and/or CD16– containing immunoreaction product is desired.

Diagnostic Systems and Kits

A diagnostic system in kit form of the present invention includes, in an amount sufficient for at least one assay, a polypeptide, antibody composition or monoclonal antibody composition of the present invention, as a packaged reagent. Instructions for use of the packaged reagent are also typically included.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalene-sulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An examplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such as $^{111}$indium or $^{3}$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol., Vol. 8 Suppl. 7:7-23 (1978), Rodwell et al., Biotech., 3:889-894 (1984), and U.S. Pat. No. 4,493,795, which are all incorporated herein by reference.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, S. aureus protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of CD163 and/or CD16 in a body fluid sample such as serum, plasma, or urine, etc. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in preferred embodiments, a polypeptide, antibody molecule composition or monoclonal antibody molecule composition of the present invention can be affixed to a solid matrix to form a solid support that comprises a package in the subject diagnostic systems.

The reagent is typically affixed to the solid matrix by adsorption from an aqueous medium although other modes of affixation, well known to those skilled in the art, can be used.

Useful solid matrices are also well known in the art. Such materials are water insoluble and include cross-linked dextral); agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

In one embodiment a diagnostic system of the present invention is useful for assaying for the presence of CD163 and/or CD16. Such a system comprises, in kit form, a package containing an antibody to CD163 and/or CD16.

Diagnostic Use

In another embodiment of the present invention, measurement of CD16 or CD163, or proteins which are immunologically related to CD16 or CD163, can be used to detect and/or stage a disease or disorder in a subject. The measured amount of the soluble molecule or of the total marker is compared to a baseline level. This baseline level can be the amount which is established to be normally present in the body fluid of subjects with various degrees of the disease or disorder. An amount present in the body 'fluid of the subject which is similar to a standard amount, established to be normally present in the body fluid of the subject during a specific stage of the disease or disorder, is indicative of the stage of the disease in the subject. The baseline level could also be the level present in the subject prior to the onset of disease or the amount present during remission of disease, or from individuals not afflicted with the disease or condition.

The present invention also provides for the detection or diagnosis of disease or the monitoring of treatment by measuring the amounts of CD16 and/or CD163 in a sample before and after treatment, and comparing the two measurements. The change in the levels of the markers relative to one another can be an improved prognostic indicator. A comparison of the amounts of a total marker with the amount of intra-cytoplasmic marker or membrane-bound marker is also envisioned.

The present invention provides a method for monitoring the effect of a therapeutic treatment on a subject who has undergone the therapeutic treatment. This method comprises measuring at suitable time intervals the amount of a soluble molecule or soluble fragment thereof, or the amount of CD16 and/or CD163 or fragment thereof. Any change or absence of change in the amount of the soluble molecule or in the amount of the CD16 and/or CD163 can be identified and correlated with the effect of the treatment on the subject. In a specific embodiment of the invention, soluble molecules immunologically related to CD16 and/or CD163 can be measured in the serum of patients by a sandwich enzyme immunoassay (for an example) in order to predict disease prognosis, for example, in HIV infection, AIDS, HIVE, HIVD, or to monitor the effectiveness of treatments such as anti-retroviral administration.

Anti-Retroviral Therapy

For purposes of the present invention, antiretroviral agents include any substance that can inhibit, reduce, or eliminate retroviral infection of a cell. A number of these agents are commercially available for administration according to the manufacturer's recommended dosage. Such antiretroviral agents include, but are not limited to, the two classes known as reverse transcriptase inhibitors and protease inhibitors, as well as agents that are inhibitors of viral entry, and combinations thereof.

A number of reverse transcriptase inhibitors are commercially available. Examples include, but are not limited to, nucleoside analogs, which are a class of compounds that are known to inhibit HIV, and non-nucleoside drugs. Nucleoside analogs are exemplified by didanosine (2',3'-dideoxyinosine or [ddI], available as Videx® from Bristol Myers-Squibb, Wallingford, Conn.); zidovudine (3'-azido-2',3'-dideoxythymidine or azidothymidine [AZT], available from Glaxo-Wellcome Co., Research Triangle Park, N.C.); zalcitabine (2',3'-dideoxycytidine [ddC], available as Hivid® from Hoffman-La Roche, Basel, Switzerland); lamivudine 2'-deoxy-3'-thiacytidine [3TC] (Epivir®, available from Glaxo-Wellcome Co.); stavudine (2',3'-didehydro-2',3'-dideoxythimidine [D4T] available as Zerit®) from Bristol Myers-Squibb); and the combination drug zidovudine plus lamivudine (Combivir®, available from Glaxo Wellcome). These particular drugs belong to the class of compounds known as 2',3'-dideoxynucleoside analogs, which, with some exceptions such as 2',3'-dideoxyuridine EDDU], are known to inhibit HIV replication, but have not been reported to clear any individual of the virus. Other nucleoside reverse transcriptase inhibitors include abacavir (1592U89, Ziagen™, available from Glaxo-Wellcome Co.). Non-nucleoside reverse transcriptase inhibitors include nevirapine (Viramune™, available from Boehringer Ingelheim Pharmaceuticals, Inc.); delaviridine (Rescriptor®, available from Pharmacia & Upjohn, Kalamazoo, Mich.); and efavirenz (available as Sustiva®, from DuPont Merck).

Examples of protease inhibitors useful in the present invention include, but are not limited to, Indinavir sulfate (available as Crixivan™ capsules from Merck & Co., inc., West Point, Pa.), saquinavir (Invirase® and Fortovase®, available from Hoffman-La Roche), ritonavir (Norvir®, available from Abbott Laboratories, Abbott Park, Ill.); ABT-378 (new name: lopinavir, available from Abbott Laboratories); Amprenavir (Agenerase™, available from Glaxo Wellcome, Inc.); and Nelfinavir (Viracept®), and GW141 (available from Glaxo Welicome/Vertex). Such examples of reverse transcriptase and protease inhibitors are not intended to be limiting. It is recognized that any known inhibitor, as well as those under development, may be used in the methods of the invention. See, for example, the drugs for HIV infection disclosed in Medical Letter 42 (Jan. 10, 2000):1-6, incorporated by reference.

Suitable human dosages for these compounds can vary widely. However, such dosages can readily be determined by those of skill in the art. Therapeutically effective amounts of these drugs are administered. By "therapeutically effective amount" is intended an amount of the antiretroviral agent that is sufficient to decrease the effects of HIV infection, or an amount that is sufficient to favorably influence the pharmacokinetic profile of one or more of the other antiretroviral agents used. Decrease in dosage frequency can be advantageous for antiretroviral agents having undesirable side effects when administered in the absence of the antiretroviral agent that increases their bioavailability.

In one embodiment, an antiretroviral agent, when administered in a therapeutically effective amount to an HIV-infected subject, decreases the effects of HIV infection by, for example, inhibiting replication of HIV, thereby decreasing viral load in the subject undergoing antiretroviral therapy. In another embodiment, an antiretroviral agent, when administered in a therapeutically effective amount to an HIV-infected subject, favorably influences the pharmacokinetics of one or more of the other antiretroviral agents used.

Guidance as to dosages for any given antiretroviral agent is available in the art and includes administering commercially available agents at their recommended dosages. See, for example, Medical Letter 42 (Jan. 10, 2000):1-6, herein incorporated by reference.

The invention will be illustrated in more detail with reference to the following Examples, but it should be understood that the present invention is not deemed to be limited thereto.

EXAMPLES

Example 1

Figure 1:
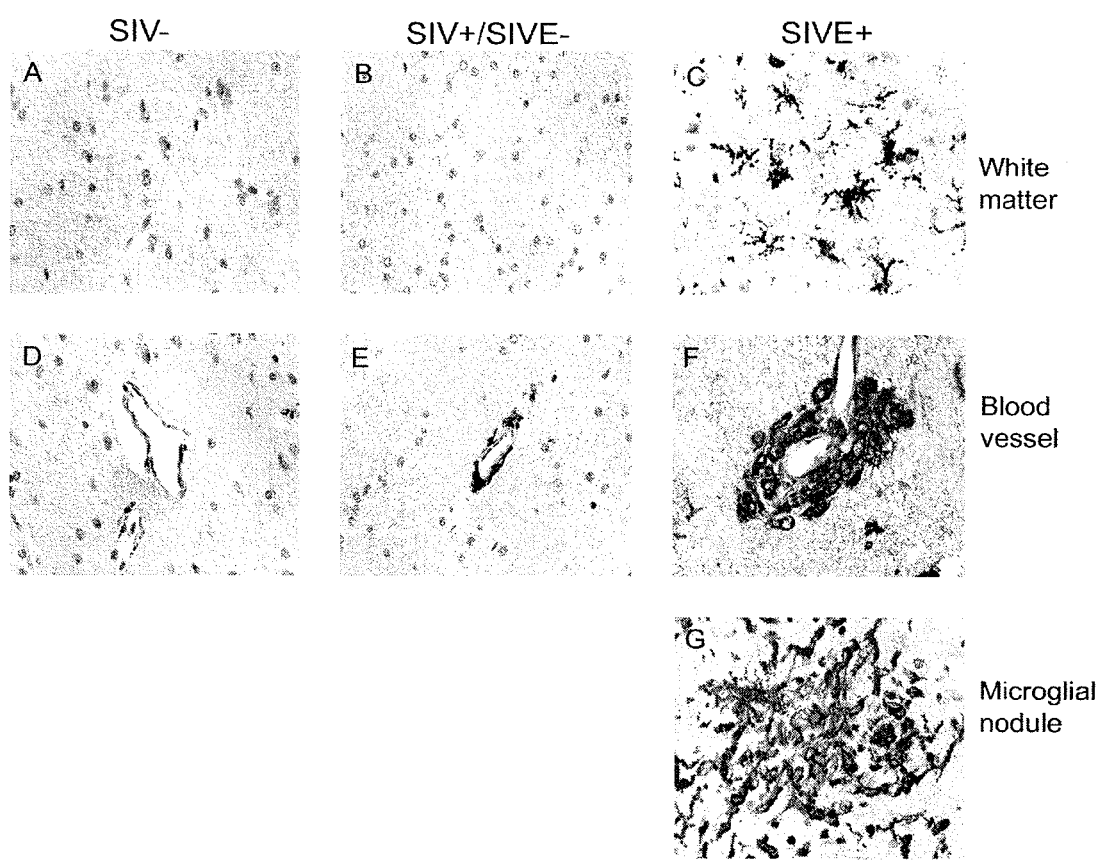
FIG. 1 illustrates that the CNS shows significant accumulation of CD163+ cells in SIV.

CNS shows significant accumulation of CD163+ cells in SIV. Referring to FIG. 1, FIG. 1A and FIG. 1D show frontal white matter from a SIy seronegative Rhesus macaque. FIG. 1B and FIG. 1E are SIVmac251 infection without encephalopathy. FIG. 1C, FIG. 1F and FIG. 1G are from SIVE. The top row (FIG. 1A, FIG. 1B, and FIG. 1C) illustrates parenchyma. FIG. 1D, FIG. 1E and FIG. 1F show blood vessels. FIG. 1G shows a microglial nodule. All panels are shown at 40× magnification. A significant number of CD163+MPs are observed in SIVE (FIG. 1C, FIG. 1F and FIG. 1G) when compared to SIV infected animals without encephalopathy (FIG. 1B and FIG. 1E) and seronegative controls (FIG. 1A and FIG. 1D). A greater accumulation of CD163+ perivascular macrophages is observed in SIV infected animals without encephalopathy (FIG. 1E) as compared to seronegative animals (FIG. 1D), however this is significantly lesser than that observed in SIVE (FIG. 1F). In SIVE, CD163+ macrophages comprise perivascular cuffs (FIG. 1F) as well as microglial nodules (FIG. 1G). Furthermore, in stark contrast to the control groups, numerous CD163+ ramified microglia are observed in the brain parenchyma (FIG. 1C).

Example 2

Figure 2:
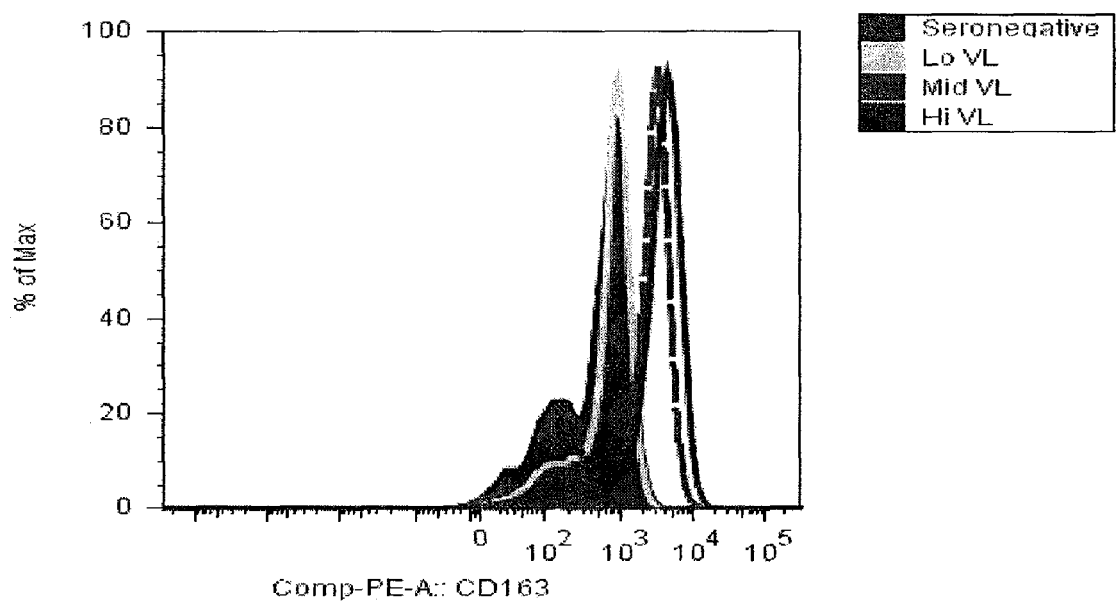
FIG. 2 illustrates that CD163 mean fluorescence intensity (MFI) increases with viral load. Peripheral blood mononuclear cells (PBMC) were isolated from whole blood of 4 seronegative and 14 SIVmac251 infected Rhesus macaques and analyzed for CD163 expression by flow cytometry. The monocyte population was first identified by CM 4 expression. This population was then further analyzed for CD163 expression, which revealed low and high CD163 expressing monocyte populations. CD163 was increased in animals with a moderate to high viral load, as demonstrated by increased MFI of CD163-PE.

CD163 mean fluorescence intensity (MFI) increases with viral load. Referring to FIG. 2, peripheral blood mononuclear cells (PBMC) were isolated from whole blood of 4 seronegative and 14 SIVmac251 infected Rhesus macaques and analyzed for eD163 expression by flow cytometry. The monocyte population was first identified by CD14 expression. This population was then further analyzed for CD163 expression, which revealed low and high CD163 expressing monocyte populations. While CD163 is reportedly expressed by all circulating monocytes, we observed that this was increased in animals with a moderate to high viral load, as demonstrated by increased MFI of CD163-PE. Anti-CD163 antibody MAC-158 (Trillium Diagnostics, Inc.).

Example 3

Figure 3:
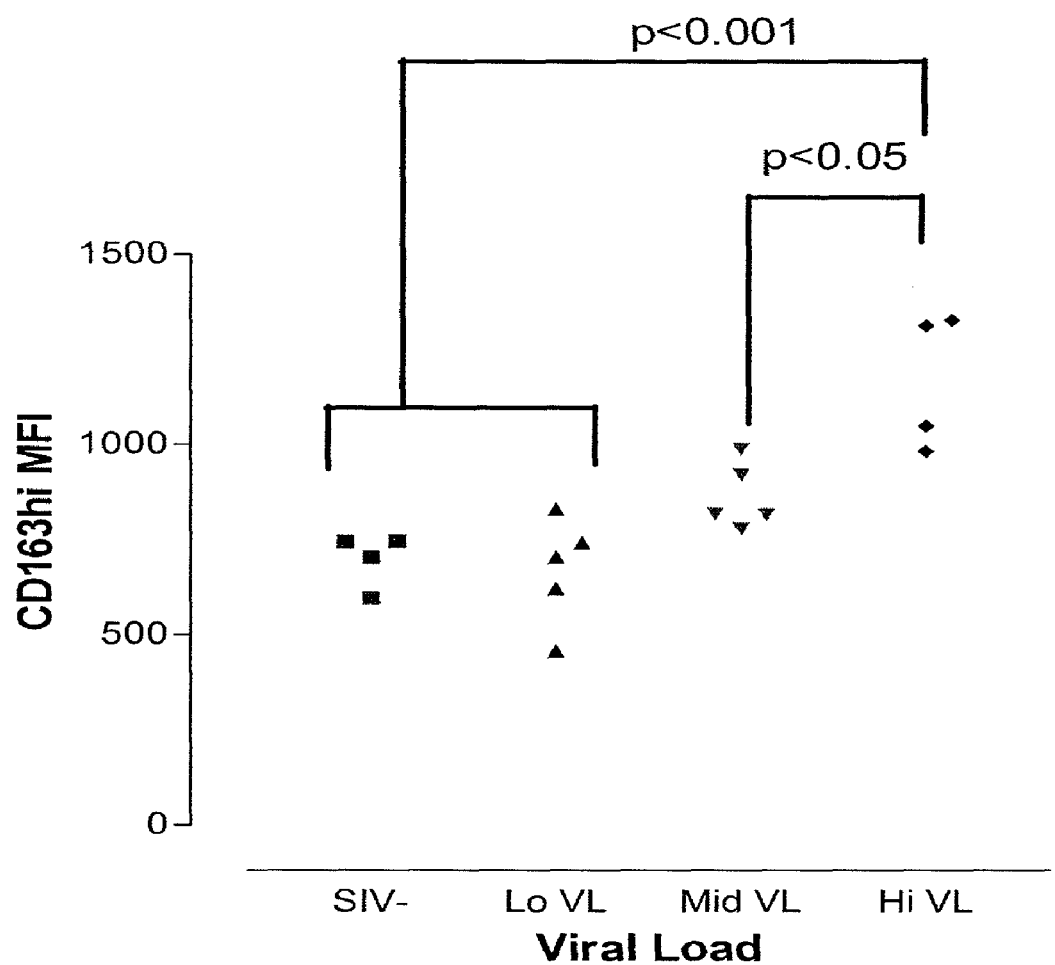
FIG. 3 illustrates that CD163hi mean fluorescence intensity MFI is significantly greater in Rhesus macaques with high viral load. Analysis of variance (ANOVA) statistical test revealed that peripheral blood monocytes from SIVmac251 infected Rhesus macaques with a high viral load have significantly greater CD163 expression than animals with a mid viral load (p<0.05) and low viral load and seronegative animals (p<0.001), as determined by MFI.

CD163hi MFI is significantly greater in Rhesus macaques with high viral load. Referring to FIG. 3, analysis of variance (ANOVA) statistical test revealed that peripheral blood monocytes from SIVmac251 infected Rhesus macaques with a high viral load have significantly greater CD163 expression than animals with a mid viral load (p<0.05) and low viral load and seronegative animals (p<0.001), as determined by MFI. Results for all comparisons were verified by the Tukey-Kramer comparison of means post-test.

Example 4

Figure 4:
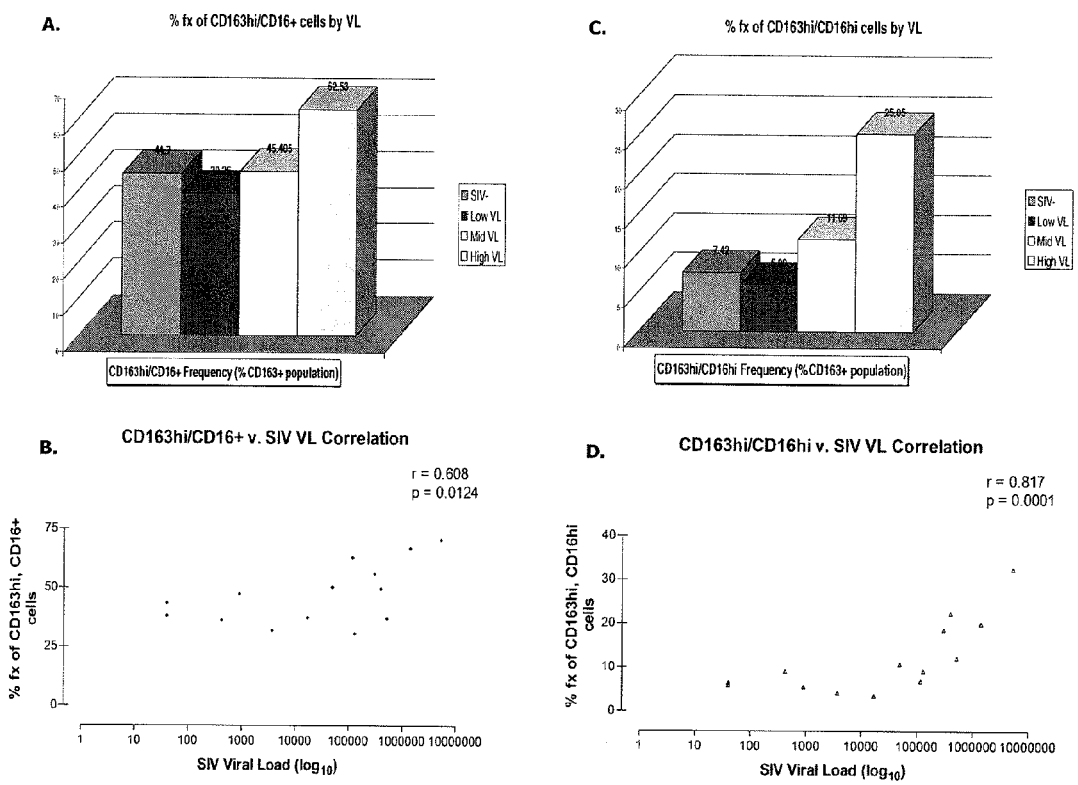
FIG. 4 illustrates that CD163hi/CD16+ and CD163hi/CD16hi monocytes are seen with a greater frequency in SIV infected Rhesus macaques with high viral load and correlate with the degree of viral burden. PBMC were isolated from whole blood of 4 seronegative and 14 SIVmac251 infected Rhesus macaques and analyzed by flow cytometer. The monocyte population was first identified by CD14 expression. This population was then further analyzed for CD163 and CD16 expression. Animals with a high viral load demonstrated a greater frequency of CD163hi/CD16+ cells as compared to animals with moderate or low viral loads and seronegative animals (FIG. 4A). Furthermore, the frequency of these cells was found to correlate with viral load (i=0.608, p=0.0124) (FIG. 4B). Greater significance was observed, however, when analyzing the CD163hi/CD16hi sub-population. This revealed a greater than 2-fold increase in the frequency of CD163hi/CD16hi monocytes from animals with a high viral load over those with a moderate viral load, with an even greater increase over those with a low viral load and seronegative animals (FIG. 4C). Moreover, a significant positive con-elation was observed with the frequency of CD163hi/CD16hi monocytes and viral burden (r.0.817, p=0.0001) (FIG. 4D).

CD163hi/CD16+ and CD163hi/CD16hi monocytes are seen with a greater frequency in SIV infected Rhesus macaques with high viral load and correlate with the degree of viral burden. PBMC were isolated from whole blood of 4 seronegative and 14 S1Vmac251 infected Rhesus macaques and analyzed by flow cytometer. The monocyte population was first identified by CD14 expression. This population was then further analyzed for CD163 and CD16 expression. Animals with a high viral load demonstrated a greater frequency of CD163hi/CD16+ cells as compared to animals with moderate or low viral loads and seronegative animals (see FIG. 4A). Furthermore, the frequency of these cells was found to correlate with viral load (i.0.608, p=0.0124) (see FIG. 4B). Greater significance was observed, however, when analyzing the CD163hi/CD16hi sub-population. This revealed a greater than 2-fold increase in the frequency of CD163hi/CD16hi monocytes from animals with a high viral load over those with a moderate viral load, with an even greater increase over those with a low viral load and seronegative animals (see FIG. 4C). Moreover, a significant positive correlation was observed with the frequency of CD163hi/CD16hi monocytes and viral burden (r=0.817, p. 0.0001) (see FIG. 4D).

Example 5

The CD16+ monocyte subset is expanded in HIV-1 infected individuals with a detectable viral load. We performed flow cytometric studies on 6 HIV- and 19 HIV+ volunteers for the expression of specific monocyte/macrophage receptors to identify receptors we hypothesized may be altered in the context of HIV-1 infection. The HIV+ volunteers, outlined in Table 1, were further grouped by viral load and included 9 volunteers successfully treated with antiretrovirals with an undetectable viral load ("suppressed"), 7 with a mid viral load (<100,000 copies/ml) and 3 with a high viral load (>100,000 copies/m.1). Anti-CD16 antibody 3G8 (BD Biosciences, Inc.).

Figure 5:
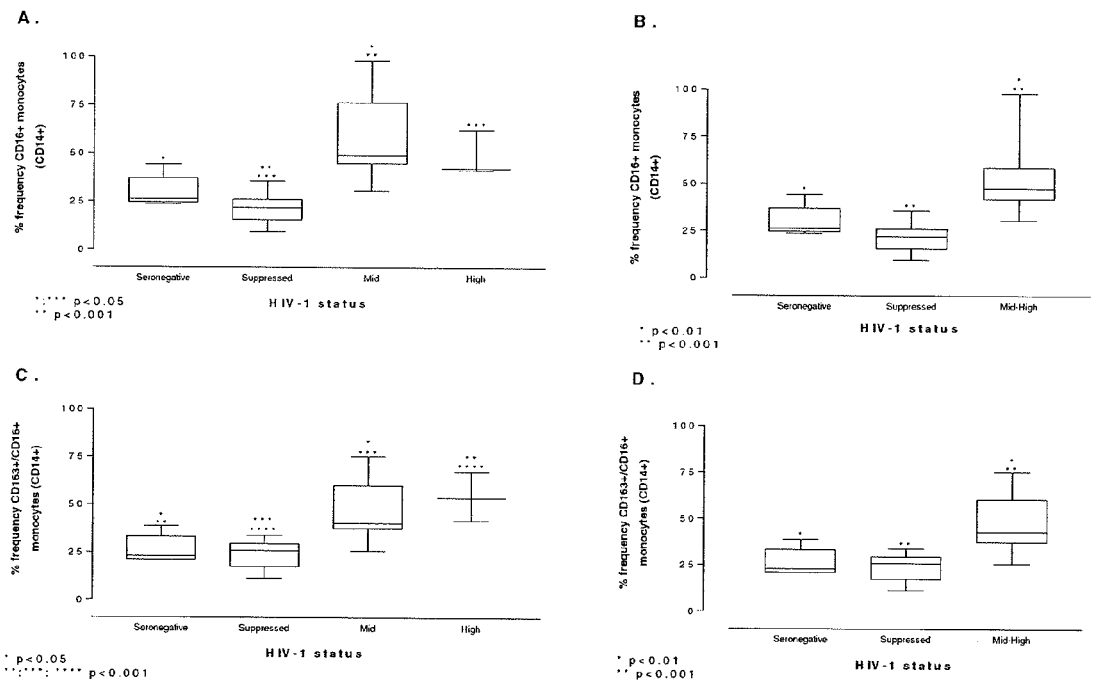
FIG. 5 illustrates that the CD16+ monocyte subset is expanded in HIV-1 infected individuals with a detectable viral load. One-way analysis of variance (ANOVA) of data obtained by flow cytometry revealed that HIV-1 infected donors with or without AIDS have a statistically significant increase in the frequency of monocytes that express CD16 as compared to seronegative donors, but only in individuals with a detectable viral load (FIG. 5A and FIG. 5B). Interestingly, individuals with an undetectable viral load (designated as "suppressed") show a small decrease in the frequency of CD16+ monocytes from that observed in seronegative donors, however this difference is not significant (FIG. 5A and FIG. 5B).

Referring to FIG. 5, one-way analysis of variance (ANOVA) of data obtained by flow cytometry revealed that HIV-1 infected donors with or without AIDS have a statistically significant increase in the frequency of monocytes that express CD16 as compared to seronegative donors, but only in individuals with a detectable viral load (FIG. 5, Panels A and B). Interestingly, individuals with an undetectable viral load (designated as "suppressed") show a small decrease in the frequency of CD16+ monocytes from that observed in seronegative donors, however this difference is not significant (FIG. 5, Panels A and B). The percent frequency of CD16+ monocytes is significantly higher in patients with mid HIV-1 viral loads relative to seronegative donors, but this difference was not significant when comparing the high viral load and seronegative groups (FIG. 5, Panel A). This is most likely the result of a low number of donors in the high viral load group (n=3). In support of this notion, combining the mid and high viral load groups such that the groups are HIV-1 (seronegative), HIV-1+ with undetectable viral load (suppressed) and HIV-1+ with a detectable viral load (mid-high) results in an even lower P value when comparing the seronegative donors and those with detectable virus (FIG. 5, Panel B).

Example 6

The CD163+/CD16 monocyte subset is expanded in HIV-1 infected donors with a detectable viral load and correlates more closely with viral load than the CD16+ monocyte subset. The percent monocyte frequency identified by CD14 expression that co-express CD163 and CD16 is increased in donors with mid and high viral loads, compared to volunteers with virus suppression and seronegative donors (FIG. 5, Panel C). Similar to the CD16+ monocyte subset, we observed a decrease in the frequency of CD163+/CD16+ monocytes in patients with virus suppression (FIG. 5, Panels C and D). This is not due solely to CD16 expression but also involves a lower percent frequency of CD163+ cells. A small decrease in CD163+ monocytes is observed approximately to the same degree among all groupings of HIV-1 infected individuals but is not significantly reduced as compared to seronegative individuals (data not shown). In contrast to our observations with the CD16+ monocyte subset, expansion of the CD163+/CD16+ monocyte subset in donors with high viral loads was significantly increased over seronegative controls (p<0.05) (FIG. 5, Panel C). Furthermore, the comparison between the fraction of the CD163+/CD16+ subset in donors with HIV-1 infection and mid viral load (FIG. 5, Panel C) and seronegative donors exhibited increased significance than when compared to CD16+ monocytes without CD163 (p<0.001 with CD163 vs p<0.05 without CD163 sub-typing). Combining the mid and high viral load groups results in a small increase in the median but does not improve the significance (FIG. 5, Panel D). Interestingly, HIV-1 infected individuals with mid to high viral loads show greater variation in CD16+ versus CD163+/CD16+ monocyte subset frequency (compare FIG. 5B mid-high with FIG. 5D mid-high), suggesting a more consistent expansion of this latter monocyte subset among patients with detectable viremia.

Example 7

The percent frequency of CD163+/CD16+ monocytes correlates with viral load in HIV-1 infected individuals. Correlation statistics were carried out on flow data obtained from HIV-1 infected individuals to determine the relationship between absolute number of CD4+ T cells, viral load and percent frequency of CD16+ and CD16+/CD163+ monocytes. A reduction in CD4+ T cells with increased viral load was observed, however, this correlation did not reach significance (FIG. 6, Panel A). Conversely, the percent frequency of CD14+/CD16+ monocytes appears to increase with increased viral burden, however, like CD4+ T cells, this relationship did not reach statistical significance (FIG. 6, Panel B). The frequency of CD163+/CD16+ monocytes also increases with viral load (FIG. 6, Panel C), however, unlike both CD4+ T cells and CD14+/CD16+ monocytes, the correlation between the frequency of CD163+/CD16+ monocytes and viral burden is statistically significant (FIG. 6, Panel C), r=0.54; p=0.018, suggesting a relationship with virus production and the expansion of this monocyte subset.

Example 8

The expansion of both CD16+ monocyte subsets correlates with CD4+ T cell depletion. Correlation statistics were also performed to determine the relationship between absolute number of CD4+ T cells and percent frequency of CD16+ and CD163+/CD16+ monocytes. A trend toward a decrease in the absolute number of CD4+ T cells with increased CD16+ and CD163+/CD16+ monocyte frequencies was observed in all HIV-1 infected individuals, however this was not significant for either monocyte subset (FIG. 7, Panels A and C). Interestingly, patients with CD4+ T cell counts below 450 cells/µl show a significant inverse correlation between CD4+ T cells and CD16+ or CD163+/CD16+(FIG. 7, Panels B and D). While both monocyte subsets do correlate well with a loss of CD4+ T cells in HIV-I infected persons with counts less than 450 cells/µi, the correlation between CD163+/CD16+ monocyte subset frequency and CD4+ T cell loss is better than that seen with the CD16+ monocyte (compare FIG. 7, Panel A r=0.26 with C r=0.31) as well as in those with CD4+ T cells below 450 cells/0 (compare FIG. 7, Panel B r=0.71 with D r=0.86).

Example 9

Expansion of the CD163+/CD16+ monocyte subset may develop from CD163+/CD16− monocytes. To begin to understand the observed expansion of the CD163+/CD16+ monocyte subset in HIV-1 infection, we investigated differences in all four CD163±/CD16±monocyte populations for divergences in the frequencies of any of these populations among the seronegative and HIV-1 infection with or without virus suppression groups. CD163/CD16+ and CD163/CD16 populations were not significantly altered in any of the groups examined (data not shown). In contrast, the frequency of CD163+/CD16− monocytes is greater in seronegative individuals and those with virus suppression than HIV-1 infected donors with mid or high viral loads (FIG. 8, Panel A). The frequency of CD163+/CD16− monocytes showed a strong inverse correlation with the frequency of CD163+/CD16+ monocytes (FIG. 8, Panel B), suggesting that these two subsets are associated and possibly the CD163+/CD16+ monocyte subset is derived from CD163+/CD16− monocytes. A strong trend toward a decrease of this monocyte subset with increased viral load (p=0.07) was observed among all HIV-I infected individuals enrolled in the study (FIG. 8, Panel C). A highly significant inverse correlation with r=0.66 and c=0.003 was observed (FIG. 8, Panel C). A positive trend toward a greater number of CD4+ T cells with increased CD163+/CD16− monocyte frequency that is not statistically significant until CD4+ T cells drop below 450 cells/µi was observed (FIG. 8, Panel D).

Example 10

Donor Enrollment

Twenty-five age (seronegative mean age=44; HIV-1+ mean age=47) and sex-matched seronegative and HIV-1 infected donors (6 HIV-1 and 19 HIV-1+) were enrolled in this study. HIV-1+ donors were grouped by viral load and included HIV-1 infected individuals with undetectable viral load, those with a mid viral load (<=100,000 copies/ml) and those with a high viral load (>100,000 copies/ml). All donors with undetectable and one with detectable (mid) viral loads were on antiretroviral therapy (ARV) at the time of the blood draw. Two of three donors with high and two of seven with mid viral loads were naïve to ARV (Table 1). Two HIV-1 infected donors were recognized as also having AIDS as defined by a CD4+ T cell count<200 cells/µl. 10 ml of blood was collected in heparin containing vaccutainer collection tubes by a qualified phlebotomist. Willing subjects were provided with and required to sign a "Consent to Participate in a Research Study" which included information regarding the purpose and description of the study as well as possible risks prior to enrollment. These studies were performed under the approval of the Temple University Institutional Review Board for Human Subjects.

Example 11

PBMC Isolation

Human peripheral blood mononuclear cells (PBMC) were isolated from heparinized whole blood within four hours of collection using a Ficoll gradient. 10 ml of diluted whole blood was layered over Ficoll (Sigma) and centrifuged at

Example 12

Flow Cytometry

Human PBMC (1×10$^6$ cells/test) were washed with FACS wash (FW) (Hank's Balanced Salt Solution containing 3% heat-inactivated FBS and 0.02% NaN3) and incubated with the following pre-titrated human fluorochrome conjugated antibodies: CD4 (clone RPAT4); CD14 (clone M532); CD16 (clone 3G8); CD69 (clone FN50); CD115 (R&D Systems, clone 61708); CD163 (Trillium Diagnostics, clone Mac2158); CCR5 (clone 3A9); CXCR4 (eBioscience, clone 12G5). All antibodies were purchased from BD Biosciences except where indicated. After incubation with antibodies, cells were washed twice with FW and resuspended in 1% paraformaldehyde. Raw data were collected on a FACSAria (BD Biosciences) and analyzed using FlowJo version 7.1.3 software, (TreeStar). Isotype controls and fluorescence minus one (FMO) tests were performed for antibody specificity and accuracy of gating, respectively.

Example 13

CD4+ T Cell and HIV-1 Viral Load Acquisition

CD4+ T cell counts and HIV-1 viral loads were obtained from the most recent clinical records. Tests were performed under standard of clinical care by Quest Diagnostics Nichols Institute, CA. Results were provided to the laboratory with patient identifiers removed. Briefly, CD4+ T cell counts were obtained from whole blood collected in EDTA vaccutainer collection tubes by flow cytometry using a cell subset panel that included markers for helper and suppressor T cell identification. Viral loads were measured from plasma separated from cells by centrifugation immediately following collection in EDTA containing vaccutainer collection tubes. Expanded Range Quantitative PCR was performed using the Amplicor HIV-1 Monitor Test Kit, v1.5 (Roche Diagnostics, Inc).

Example 14

Statistical Analyses

One way analysis of variance (ANOVA) with Tukey-Kramer multiple comparisons post-test and correlation tests were performed on flow cytometry data using Graph Pad Prism version 3.00 software, San Diego Calif.

While the invention has been described in detail and with reference to specific examples thereof, it will be apparent to one skilled in the art that various changes and modifications can be made therein without departing from the spirit and scope thereof.

---

What is claimed is:

1. A method for determining the risk of neurological manifestations of HIV infection in an HIV-1-infected subject, comprising:
    (a) obtaining a first blood, serum, or plasma sample from the subject;
    (b) determining from the first blood, serum, or plasma sample a fraction of CD163+/CD16+ monocytes in a population of peripheral blood mononuclear cells, an HIV-1 viral load, and a CD4+ T cell count;
    (c) at a different time, obtaining a subsequent blood, serum, or plasma sample from the subject; and
    (d) determining from the subsequent blood, serum, or plasma sample a fraction of CD163+/CD16+ monocytes in a population of peripheral blood mononuclear cells, an HIV-1 viral load, and a CD4+ T cell count;
    wherein when the fractions of CD163+/CD16+ monocytes in peripheral blood mononuclear cells and the HIV-1 viral loads in steps (b) and (d) are above a baseline fraction and a baseline HIV-1 viral load in healthy seronegative subjects respectively while the CD4+ T cell counts in steps (b) and (d) are below a baseline count in healthy seronegative subjects, this is indicative of the risk of neurological manifestations of HIV infection in the HIV-1-infected subject.

2. A method for determining the risk of CNS invasion by HIV-1 virus in HIV-1-positive subjects comprising:
    (a) obtaining a first blood, serum, or plasma sample from the subject,
    (b) determining from the first blood, serum, or plasma sample a fraction of CD 163+/CD16+ monocytes in peripheral blood mononuclear cells, an HIV-1 viral load, and a CD4+ T cell count of the subject,
    (c) at a different time, obtaining a subsequent blood, serum, or plasma sample from the subject; and
    (d) determining from the subsequent blood, serum, or plasma sample a fraction of CD163+/CD16+ monocytes in peripheral blood mononuclear cells, an HIV-1 viral load, and a CD4+ T cell count of the subject;
    wherein when the fractions of CD163+/CD16+ monocytes in peripheral blood mononuclear cells and the HIV-1 viral loads in steps (b) and (d) are above a baseline fraction and a baseline HIV-1 viral load in healthy seronegative subjects respectively while the CD4+ T cell counts in steps (b) and (d) are below a baseline count in healthy seronegative subjects, this is indicative of a risk of CNS invasion by said virus.

3. A method for predicting HIV-1 disease progression in an HIV-1-positive subject comprising:
    (a) obtaining a first blood, serum, or plasma sample from the subject;

(b) determining from the first blood, serum, or plasma sample a fraction of CD 163+/CD16+ monocytes in peripheral blood mononuclear cells, an HIV-1 viral load, and a CD4+ T cell count;

(c) at a different time, obtaining a subsequent blood, serum, or plasma sample from the subject; and (d) determining from the subsequent blood, serum, or plasma sample a fraction of CD163+/CD16+ monocytes in peripheral blood mononuclear cells, an HIV-1 viral load, and a CD4+ T cell count;

wherein when the fractions of CD163+/CD16+ monocytes in peripheral blood mononuclear cells and the HIV-1 viral loads in steps (b) and (d) are above a baseline fraction and a baseline HIV-1 viral load in healthy seronegative subjects respectively while the CD4+ T cell counts in steps (b) and (d) are below a baseline count in healthy seronegative subjects, this is predictive of HIV-1 disease progression in the HIV-1-positive subject.

4. A method for monitoring a viral load of an HIV-infected subject comprising:

(a) obtaining a first blood, serum, or plasma sample from the subject;

(b) determining from the first blood, serum, or plasma sample a fraction of CD 163+/CD16+ monocytes in peripheral blood mononuclear cells;

(c) at a different time, obtaining a subsequent blood, serum, or plasma sample from the subject; and (d) determining from the subsequent blood, serum, or plasma sample a fraction of CD163+/CD16+ monocytes in peripheral blood mononuclear cells of the subject;

wherein when the fractions of CD163+/CD16+ monocytes in peripheral blood mononuclear cells in steps (b) and (d) are above a baseline fraction in healthy seronegative subjects, this is indicative of an increased HIV-1 viral load in the HIV-1-positive subject.

5. A method for determining a risk of disease progression in an HIV-infected subject comprising:

(a) obtaining a first blood, serum, or plasma sample from the subject;

(b) determining from the first blood, serum, or plasma sample a fraction of CD163+/CD16+ monocytes in peripheral blood mononuclear cells, an HIV-1 viral load, and a CD4+ T cell count;

(c) at a different time, obtaining a subsequent blood, serum, or plasma sample from the subject; and (d) determining from the subsequent blood, serum, or plasma sample a fraction of CD163+/CD16+ monocytes in peripheral blood mononuclear cells, an HIV-1 viral load, and a CD4+ T cell count of the subject;

wherein when the fractions of CD163+/CD16+ monocytes in peripheral blood mononuclear cells and the HIV-1 viral loads in steps (b) and (d) are above a baseline fraction and a baseline HIV-1 viral load in healthy seronegative subjects respectively while the CD4+ T cell counts in steps (b) and (d) are below a baseline count in healthy seronegative subjects, this is indicative of an increased risk of disease progression in the HIV-infected subject.

6. A method for determining a risk of development of HIV encephalopathy in an HIV-infected subject comprising:

(a) obtaining a first blood, serum, or plasma sample from the subject;

(b) determining from the first blood, serum, or plasma sample a fraction of CD 163+/CD16+ monocytes in peripheral blood mononuclear cells, an HIV-1 viral load, and a CD4+ T cell count;

(c) at a different time, obtaining a subsequent blood, serum, or plasma sample from the subject; and (d) determining from the subsequent blood, serum, or plasma sample a fraction of CD163+/CD16+ monocytes in peripheral blood mononuclear cells, an HIV-1 viral load, and a CD4+ T cell count;

wherein when the fractions of CD163+/CD16+ monocytes in peripheral blood mononuclear cells and the HIV-1 viral loads in steps (b) and (d) are above a baseline fraction and a baseline HIV-1 viral load in healthy seronegative subjects respectively while the CD4+ T cell counts in steps (b) and (d) are below a baseline count in healthy seronegative subjects, this is indicative of an increased risk of development of HIV encephalopathy in the HIV-infected subject.

7. The method of claim 6, wherein when the fractions of CD163+/CD16+ monocytes in peripheral blood mononuclear cells and the HIV-1 viral loads in steps (b) and (d) are above the baseline fraction and a baseline HIV-1 viral load in healthy seronegative subjects while the CD4+ T cell counts in steps (b) and (d) are below a baseline count in healthy seronegative subjects, this is further an indication that the HIV-infected subject should be treated with antiretroviral therapy.

\* \* \* \* \*

UNITED STATES PATENT AND TRADEMARK OFFICE
CERTIFICATE OF CORRECTION

| | |
|---|---|
| PATENT NO. | : 8,273,538 B2 |
| APPLICATION NO. | : 12/301796 |
| DATED | : September 25, 2012 |
| INVENTOR(S) | : Jay Rappaport and Tracy Fischer-Smith |

It is certified that error appears in the above-identified patent and that said Letters Patent is hereby corrected as shown below:

In the Specification

At Column 1, Lines 15-17, the wording "The invention described herein was supported in part by NIH/NINDS grant IRO I NSO47031. The United States government has certain rights in the invention." should read --This invention was made with government support under NS047031 awarded by the National Institutes of Health. The government has certain rights in the invention.--.

Signed and Sealed this
Seventh Day of November, 2023

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 1116
<212> TYPE: PRT
<213> ORGANISM: Homo sapiens

<400> SEQUENCE: 1

Met Val Leu Leu Glu Asp Ser Gly Ser Ala Asp Phe Arg Arg His Phe
1               5                   10                  15

Val Asn Leu Ser Pro Phe Thr Ile Thr Val Val Leu Leu Leu Ser Ala
            20                  25                  30

Cys Phe Val Thr Ser Ser Leu Gly Gly Thr Asp Lys Glu Leu Arg Leu
        35                  40                  45

Val Asp Gly Glu Asn Lys Cys Ser Gly Arg Val Glu Val Lys Val Gln
    50                  55                  60

Glu Glu Trp Gly Thr Val Cys Asn Asn Gly Trp Ser Met Glu Ala Val
65                  70                  75                  80

Ser Val Ile Cys Asn Gln Leu Gly Cys Pro Thr Ala Ile Lys Ala Pro
                85                  90                  95

Gly Trp Ala Asn Ser Ser Ala Gly Ser Gly Arg Ile Trp Met Asp His
            100                 105                 110

Val Ser Cys Arg Gly Asn Glu Ser Ala Leu Trp Asp Cys Lys His Asp
        115                 120                 125

Gly Trp Gly Lys His Ser Asn Cys Thr His Gln Gln Asp Ala Gly Val
    130                 135                 140

Thr Cys Ser Asp Gly Ser Asn Leu Glu Met Arg Leu Thr Arg Gly Gly
145                 150                 155                 160
```

```
Asn Met Cys Ser Gly Arg Ile Glu Ile Lys Phe Gln Gly Arg Trp Gly
            165                 170                 175

Thr Val Cys Asp Asp Asn Phe Asn Ile Asp His Ala Ser Val Ile Cys
            180                 185                 190

Arg Gln Leu Glu Cys Gly Ser Ala Val Ser Phe Ser Gly Ser Ser Asn
            195                 200                 205

Phe Gly Glu Gly Ser Gly Pro Ile Trp Phe Asp Asp Leu Ile Cys Asn
            210                 215                 220

Gly Asn Glu Ser Ala Leu Trp Asn Cys Lys His Gln Gly Trp Gly Lys
225                 230                 235                 240

His Asn Cys Asp His Ala Glu Asp Ala Gly Val Ile Cys Ser Lys Gly
            245                 250                 255

Ala Asp Leu Ser Leu Arg Leu Val Asp Gly Val Thr Glu Cys Ser Gly
            260                 265                 270

Arg Leu Glu Val Arg Phe Gln Gly Glu Trp Gly Thr Ile Cys Asp Asp
            275                 280                 285

Gly Trp Asp Ser Tyr Asp Ala Ala Val Ala Cys Lys Gln Leu Gly Cys
            290                 295                 300

Pro Thr Ala Val Thr Ala Ile Gly Arg Val Asn Ala Ser Lys Gly Phe
305                 310                 315                 320

Gly His Ile Trp Leu Asp Ser Val Ser Cys Gln Gly His Glu Pro Ala
            325                 330                 335

Val Trp Gln Cys Lys His His Glu Trp Gly Lys His Tyr Cys Asn His
            340                 345                 350

Asn Glu Asp Ala Gly Val Thr Cys Ser Asp Gly Ser Asp Leu Glu Leu
            355                 360                 365

Arg Leu Arg Gly Gly Gly Ser Arg Cys Ala Gly Thr Val Glu Val Glu
            370                 375                 380

Ile Gln Arg Leu Leu Gly Lys Val Cys Asp Arg Gly Trp Gly Leu Lys
385                 390                 395                 400

Glu Ala Asp Val Val Cys Arg Gln Leu Gly Cys Gly Ser Ala Leu Lys
            405                 410                 415

Thr Ser Tyr Gln Val Tyr Ser Lys Ile Gln Ala Thr Asn Thr Trp Leu
            420                 425                 430

Phe Leu Ser Ser Cys Asn Gly Asn Glu Thr Ser Leu Trp Asp Cys Lys
            435                 440                 445

Asn Trp Gln Trp Gly Gly Leu Thr Cys Asp His Tyr Glu Glu Ala Lys
450                 455                 460

Ile Thr Cys Ser Ala His Arg Glu Pro Arg Leu Val Gly Gly Asp Ile
465                 470                 475                 480

Pro Cys Ser Gly Arg Val Glu Val Lys His Gly Asp Thr Trp Gly Ser
            485                 490                 495

Ile Cys Asp Ser Asp Phe Ser Leu Glu Ala Ala Ser Val Leu Cys Arg
            500                 505                 510

Glu Leu Gln Cys Gly Thr Val Val Ser Ile Leu Gly Gly Ala His Phe
            515                 520                 525

Gly Glu Gly Asn Gly Gln Ile Trp Ala Glu Glu Phe Gln Cys Glu Gly
            530                 535                 540

His Glu Ser His Leu Ser Leu Cys Pro Val Ala Pro Arg Pro Glu Gly
545                 550                 555                 560

Thr Cys Ser His Ser Arg Asp Val Gly Val Val Cys Ser Arg Tyr Thr
            565                 570                 575

Glu Ile Arg Leu Val Asn Gly Lys Thr Pro Cys Glu Gly Arg Val Glu
            580                 585                 590
```

```
Leu Lys Thr Leu Gly Ala Trp Gly Ser Leu Cys Asn Ser His Trp Asp
        595                 600                 605
Ile Glu Asp Ala His Val Leu Cys Gln Gln Leu Lys Cys Gly Val Ala
610                 615                 620
Leu Ser Thr Pro Gly Gly Ala Arg Phe Gly Lys Gly Asn Gly Gln Ile
625                 630                 635                 640
Trp Arg His Met Phe His Cys Thr Gly Thr Glu Gln His Met Gly Asp
                    645                 650                 655
Cys Pro Val Thr Ala Leu Gly Ala Ser Leu Cys Pro Ser Glu Gln Val
                660                 665                 670
Ala Ser Val Ile Cys Ser Gly Asn Gln Ser Gln Thr Leu Ser Ser Cys
            675                 680                 685
Asn Ser Ser Leu Gly Pro Thr Arg Pro Thr Ile Pro Glu Glu Ser
        690                 695                 700
Ala Val Ala Cys Ile Glu Ser Gly Gln Leu Arg Leu Val Asn Gly Gly
705                 710                 715                 720
Gly Arg Cys Ala Gly Arg Val Glu Ile Tyr His Glu Gly Ser Trp Gly
                    725                 730                 735
Thr Ile Cys Asp Asp Ser Trp Asp Leu Ser Asp Ala His Val Val Cys
                740                 745                 750
Arg Gln Leu Gly Cys Gly Glu Ala Ile Asn Ala Thr Gly Ser Ala His
            755                 760                 765
Phe Gly Glu Gly Thr Gly Pro Ile Trp Leu Asp Glu Met Lys Cys Asn
        770                 775                 780
Gly Lys Glu Ser Arg Ile Trp Gln Cys His Ser His Gly Trp Gly Gln
785                 790                 795                 800
Gln Asn Cys Arg His Lys Glu Asp Ala Gly Val Ile Cys Ser Glu Phe
                    805                 810                 815
Met Ser Leu Arg Leu Thr Ser Glu Ala Ser Arg Glu Ala Cys Ala Gly
                820                 825                 830
Arg Leu Glu Val Phe Tyr Asn Gly Ala Trp Gly Thr Val Gly Lys Ser
            835                 840                 845
Ser Met Ser Glu Thr Thr Val Gly Val Val Cys Arg Gln Leu Gly Cys
        850                 855                 860
Ala Asp Lys Gly Lys Ile Asn Pro Ala Ser Leu Asp Lys Ala Met Ser
865                 870                 875                 880
Ile Pro Met Trp Val Asp Asn Val Gln Cys Pro Lys Gly Pro Asp Thr
                    885                 890                 895
Leu Trp Gln Cys Pro Ser Ser Pro Trp Glu Lys Arg Leu Ala Ser Pro
                900                 905                 910
Ser Glu Glu Thr Trp Ile Thr Cys Asp Asn Lys Ile Arg Leu Gln Glu
            915                 920                 925
Gly Pro Thr Ser Cys Ser Gly Arg Val Glu Ile Trp His Gly Gly Ser
        930                 935                 940
Trp Gly Thr Val Cys Asp Asp Ser Trp Asp Leu Asp Asp Ala Gln Val
945                 950                 955                 960
Val Cys Gln Gln Leu Gly Cys Gly Pro Ala Leu Lys Ala Phe Lys Glu
                    965                 970                 975
Ala Glu Phe Gly Gln Gly Thr Gly Pro Ile Trp Leu Asn Glu Val Lys
                980                 985                 990
Cys Lys Gly Asn Glu Ser Ser Leu Trp Asp Cys Pro Ala Arg Arg Trp
            995                 1000                1005
Gly His Ser Glu Cys Gly His Lys Glu Asp Ala Ala Val Asn Cys
```

```
                1010                1015                1020
Thr Asp Ile Ser Val Gln Lys Thr Pro Gln Lys Ala Thr Thr Gly
    1025                1030                1035

Arg Ser Ser Arg Gln Ser Ser Phe Ile Ala Val Gly Ile Leu Gly
    1040                1045                1050

Val Val Leu Leu Ala Ile Phe Val Ala Leu Phe Phe Leu Thr Lys
    1055                1060                1065

Lys Arg Arg Gln Arg Gln Arg Leu Ala Val Ser Ser Arg Gly Glu
    1070                1075                1080

Asn Leu Val His Gln Ile Gln Tyr Arg Glu Met Asn Ser Cys Leu
    1085                1090                1095

Asn Ala Asp Asp Leu Asp Leu Met Asn Ser Ser Gly Gly His Ser
    1100                1105                1110

Glu Pro His
    1115

<210> SEQ ID NO 2
<211> LENGTH: 921
<212> TYPE: PRT
<213> ORGANISM: Homo sapiens

<400> SEQUENCE: 2

Met Asn Ala Pro Glu Arg Gln Pro Gln Pro Asp Gly Gly Asp Ala Pro
1               5                   10                  15

Gly His Glu Pro Gly Gly Ser Pro Gln Asp Glu Leu Asp Phe Ser Ile
                20                  25                  30

Leu Phe Asp Tyr Glu Tyr Leu Asn Pro Asn Glu Glu Glu Pro Asn Ala
            35                  40                  45

His Lys Val Ala Ser Pro Pro Ser Gly Pro Ala Tyr Pro Asp Asp Val
        50                  55                  60

Leu Asp Tyr Gly Leu Lys Pro Tyr Ser Pro Leu Ala Ser Leu Ser Gly
65                  70                  75                  80

Glu Pro Pro Gly Arg Phe Gly Glu Pro Asp Arg Val Gly Pro Gln Lys
                    85                  90                  95

Phe Leu Ser Ala Ala Lys Pro Ala Gly Ala Ser Gly Leu Ser Pro Arg
                100                 105                 110

Ile Glu Ile Thr Pro Ser His Glu Leu Ile Gln Ala Val Gly Pro Leu
            115                 120                 125

Arg Met Arg Asp Ala Gly Leu Leu Val Glu Gln Pro Pro Leu Ala Gly
        130                 135                 140

Val Ala Ala Ser Pro Arg Phe Thr Leu Pro Val Pro Gly Phe Glu Gly
145                 150                 155                 160

Tyr Arg Glu Pro Leu Cys Leu Ser Pro Ala Ser Ser Gly Ser Ser Ala
                    165                 170                 175

Ser Phe Ile Ser Asp Thr Phe Ser Pro Tyr Thr Ser Pro Cys Val Ser
                180                 185                 190

Pro Asn Asn Gly Gly Pro Asp Asp Leu Cys Pro Gln Phe Gln Asn Ile
            195                 200                 205

Pro Ala His Tyr Ser Pro Arg Thr Ser Pro Ile Met Ser Pro Arg Thr
        210                 215                 220

Ser Leu Ala Glu Asp Ser Cys Leu Gly Arg His Ser Pro Val Pro Arg
225                 230                 235                 240

Pro Ala Ser Arg Ser Ser Ser Pro Gly Ala Lys Arg Arg His Ser Cys
                    245                 250                 255

Ala Glu Ala Leu Val Ala Leu Pro Pro Gly Ala Ser Pro Gln Arg Ser
```

```
                260                 265                 270
Arg Ser Pro Ser Pro Gln Pro Ser His Val Ala Pro Gln Asp His
        275                 280                 285
Gly Ser Pro Ala Gly Tyr Pro Pro Val Ala Gly Ser Ala Val Ile Met
        290                 295                 300
Asp Ala Leu Asn Ser Leu Ala Thr Asp Ser Pro Cys Gly Ile Pro Pro
305                 310                 315                 320
Lys Met Trp Lys Thr Ser Pro Asp Pro Ser Pro Val Ser Ala Ala Pro
                325                 330                 335
Ser Lys Ala Gly Leu Pro Arg His Ile Tyr Pro Ala Val Glu Phe Leu
        340                 345                 350
Gly Pro Cys Glu Gln Gly Glu Arg Arg Asn Ser Ala Pro Glu Ser Ile
        355                 360                 365
Leu Leu Val Pro Pro Thr Trp Pro Lys Pro Leu Val Pro Ala Ile Pro
        370                 375                 380
Ile Cys Ser Ile Pro Val Thr Ala Ser Leu Pro Pro Leu Glu Trp Pro
385                 390                 395                 400
Leu Ser Ser Gln Ser Gly Ser Tyr Glu Leu Arg Ile Glu Val Gln Pro
                405                 410                 415
Lys Pro His His Arg Ala His Tyr Glu Thr Glu Gly Ser Arg Gly Ala
        420                 425                 430
Val Lys Ala Pro Thr Gly Gly His Pro Val Val Gln Leu His Gly Tyr
        435                 440                 445
Met Glu Asn Lys Pro Leu Gly Leu Gln Ile Phe Ile Gly Thr Ala Asp
        450                 455                 460
Glu Arg Ile Leu Lys Pro His Ala Phe Tyr Gln Val His Arg Ile Thr
465                 470                 475                 480
Gly Lys Thr Val Thr Thr Thr Ser Tyr Glu Lys Ile Val Gly Asn Thr
                485                 490                 495
Lys Val Leu Glu Ile Pro Leu Glu Pro Lys Asn Asn Met Arg Ala Thr
        500                 505                 510
Ile Asp Cys Ala Gly Ile Leu Lys Leu Arg Asn Ala Asp Ile Glu Leu
        515                 520                 525
Arg Lys Gly Glu Thr Asp Ile Gly Arg Lys Asn Thr Arg Val Arg Leu
        530                 535                 540
Val Phe Arg Val His Ile Pro Glu Ser Ser Gly Arg Ile Val Ser Leu
545                 550                 555                 560
Gln Thr Ala Ser Asn Pro Ile Glu Cys Ser Gln Arg Ser Ala His Glu
                565                 570                 575
Leu Pro Met Val Glu Arg Gln Asp Thr Asp Ser Cys Leu Val Tyr Gly
                580                 585                 590
Gly Gln Gln Met Ile Leu Thr Gly Gln Asn Phe Thr Ser Glu Ser Lys
        595                 600                 605
Val Val Phe Thr Glu Lys Thr Thr Asp Gly Gln Gln Ile Trp Glu Met
        610                 615                 620
Glu Ala Thr Val Asp Lys Asp Lys Ser Gln Pro Asn Met Leu Phe Val
625                 630                 635                 640
Glu Ile Pro Glu Tyr Arg Asn Lys His Ile Arg Thr Pro Val Lys Val
                645                 650                 655
Asn Phe Tyr Val Ile Asn Gly Lys Arg Lys Arg Ser Gln Pro Gln His
                660                 665                 670
Phe Thr Tyr His Pro Val Pro Ala Ile Lys Thr Glu Pro Thr Asp Glu
        675                 680                 685
```

-continued

```
Tyr Asp Pro Thr Leu Ile Cys Ser Pro Thr His Gly Gly Leu Gly Ser
    690             695             700
Gln Pro Tyr Tyr Pro Gln His Pro Met Val Ala Glu Ser Pro Ser Cys
705             710             715             720
Leu Val Ala Thr Met Ala Pro Cys Gln Gln Phe Arg Thr Gly Leu Ser
            725             730             735
Ser Pro Asp Ala Arg Tyr Gln Gln Gln Asn Pro Ala Ala Val Leu Tyr
            740             745             750
Gln Arg Ser Lys Ser Leu Ser Pro Ser Leu Leu Gly Tyr Gln Gln Pro
            755             760             765
Ala Leu Met Ala Ala Pro Leu Ser Leu Ala Asp Ala His Arg Ser Val
    770             775             780
Leu Val His Ala Gly Ser Gln Gly Gln Ser Ser Ala Leu Leu His Pro
785             790             795             800
Ser Pro Thr Asn Gln Gln Ala Ser Pro Val Ile His Tyr Ser Pro Thr
            805             810             815
Asn Gln Gln Leu Arg Cys Gly Ser His Gln Glu Phe Gln His Ile Met
            820             825             830
Tyr Cys Glu Asn Phe Ala Pro Gly Thr Thr Arg Pro Gly Pro Pro
            835             840             845
Val Ser Gln Gly Gln Arg Leu Ser Pro Gly Ser Tyr Pro Thr Val Ile
    850             855             860
Gln Gln Gln Asn Ala Thr Ser Gln Arg Ala Ala Lys Asn Gly Pro Pro
865             870             875             880
Val Ser Asp Gln Lys Glu Val Leu Pro Ala Gly Val Thr Ile Lys Gln
            885             890             895
Glu Gln Asn Leu Asp Gln Thr Tyr Leu Asp Asp Glu Leu Ile Asp Thr
            900             905             910
His Leu Ser Trp Ile Gln Asn Ile Leu
            915             920
```